(12) United States Patent
Jackson et al.

(10) Patent No.: US 12,419,500 B2
(45) Date of Patent: Sep. 23, 2025

(54) ENDOSCOPE STORAGE CART, SYSTEM AND METHODS

(71) Applicant: Medivators Inc., Minneapolis, MN (US)

(72) Inventors: Mark Jackson, Great Wakering (GB); Stephen Nichols, Witham (GB); Lindani Phungula, Southend On Sea (GB); Colin Oxford, Canvey Island (GB); Gary Spencer, Rayleigh (GB)

(73) Assignee: Medivators Inc., Minneapolis, MN (US)

( * ) Notice: Subject to any disclaimer, the term of this patent is extended or adjusted under 35 U.S.C. 154(b) by 39 days.

(21) Appl. No.: 18/648,740

(22) Filed: Apr. 29, 2024

(65) Prior Publication Data

US 2024/0268635 A1 Aug. 15, 2024

Related U.S. Application Data

(63) Continuation of application No. 17/618,981, filed as application No. PCT/US2020/036618 on Jun. 8, 2020, now Pat. No. 11,974,721.

(60) Provisional application No. 62/864,159, filed on Jun. 20, 2019.

(51) Int. Cl.
| | |
|---|---|
| *A61B 50/00* | (2016.01) |
| *A61B 1/00* | (2006.01) |
| *A61B 50/33* | (2016.01) |
| *A61B 50/30* | (2016.01) |

(52) U.S. Cl.
CPC .......... *A61B 1/00144* (2013.01); *A61B 50/33* (2016.02); *A61B 2050/005* (2016.02); *A61B 2050/314* (2016.02)

(58) Field of Classification Search
CPC ............... A61B 1/00144; A61B 50/33; A61B 2050/005; A61B 2050/314
USPC .......................................................... 206/363
See application file for complete search history.

(56) References Cited

U.S. PATENT DOCUMENTS

| | | | |
|---|---|---|---|
| 803,102 | A | 10/1905 | Harris |
| 1,592,726 | A | 7/1926 | Dunbar |
| 1,717,974 | A | 6/1929 | Heinrichs |
| 2,080,108 | A | 5/1937 | Bradstein |
| 2,214,946 | A | 9/1940 | Werner |

(Continued)

FOREIGN PATENT DOCUMENTS

| | | |
|---|---|---|
| AU | 2018211256 A1 | 2/2019 |
| CN | 108030556 A | 5/2018 |

(Continued)

OTHER PUBLICATIONS

ARES flexible endoscope automated reprocessing system' (Steelco) Jul. 12, 2018 (Jul. 12, 2018) [retreived from the internet on Aug. 24, 2020 (Aug. 24, 2020) at https://web.archive.org/web/20180712214831/http://www.peacocks.net/_filecache/9e4/a6e/550-steelco-ares-rev04.pdf].

(Continued)

*Primary Examiner* — Jacob K Ackun

(57) ABSTRACT

A cart for storage of an endoscope is provided. The cart comprises a housing having a slot configured to slidably receive a tray. The tray is configured to store an endoscope, and a timer is coupled to the housing, slot and/or tray. The timer is configured to display increments of time that the endoscope is stored in the tray. Systems and methods are also provided.

9 Claims, 34 Drawing Sheets

(56) References Cited

U.S. PATENT DOCUMENTS

| | | |
|---|---|---|
| 2,412,325 A | 12/1946 | Devine et al. |
| 3,157,902 A | 11/1964 | Hardwick |
| 3,757,990 A | 9/1973 | Buth |
| 3,770,119 A | 11/1973 | Hultberg et al. |
| 3,949,934 A | 4/1976 | Goglio |
| 4,042,109 A | 8/1977 | Barcan |
| 4,053,280 A | 10/1977 | Salisbury |
| 4,256,225 A | 3/1981 | Jackson |
| 4,466,552 A | 8/1984 | Butterworth et al. |
| 4,574,978 A | 3/1986 | Hodges |
| 4,583,643 A | 4/1986 | Sanderson |
| 4,704,254 A | 11/1987 | Nichols |
| 4,730,729 A | 3/1988 | Harry |
| 4,750,619 A | 6/1988 | Cohen et al. |
| 4,754,595 A | 7/1988 | Sanderson |
| 4,903,718 A | 2/1990 | Sullivan |
| 4,948,266 A | 8/1990 | Bencic |
| 5,108,195 A | 4/1992 | Perron |
| 5,207,325 A | 5/1993 | Kennedy |
| 5,263,777 A | 11/1993 | Domke |
| 5,288,467 A | 2/1994 | Biermaier |
| 5,295,606 A | 3/1994 | Karwoski |
| 5,392,917 A | 2/1995 | Alpern et al. |
| 5,409,126 A | 4/1995 | Demars |
| 5,443,801 A | 8/1995 | Langford |
| 5,733,243 A | 3/1998 | Yabe et al. |
| 5,882,589 A | 3/1999 | Mariotti |
| 5,989,608 A | 11/1999 | Mizuno |
| 6,029,844 A | 2/2000 | Brady |
| 6,041,794 A | 3/2000 | Lin et al. |
| 6,139,185 A | 10/2000 | Hamilton et al. |
| 6,151,910 A | 11/2000 | Hazen |
| 6,210,638 B1 | 4/2001 | Grieco et al. |
| 6,235,692 B1 | 5/2001 | Scoville et al. |
| 6,305,567 B1 | 10/2001 | Sulpizio |
| 6,312,645 B1 | 11/2001 | Lin et al. |
| 6,378,721 B1 | 4/2002 | Williams |
| 6,380,524 B1 | 4/2002 | Keller |
| 6,622,862 B1 | 9/2003 | Corrado |
| 6,622,864 B1 | 9/2003 | Debbs et al. |
| 6,641,781 B2 | 11/2003 | Walta |
| 6,733,803 B1 | 5/2004 | Vidkjaer |
| 6,749,063 B2 | 6/2004 | Parker |
| 6,916,456 B2 | 7/2005 | Martineau et al. |
| 6,994,823 B2 | 2/2006 | Hight, III |
| 7,041,941 B2 | 5/2006 | Faries, Jr. et al. |
| D531,734 S | 11/2006 | Haunschild et al. |
| 7,132,089 B2 | 11/2006 | Lacabanne |
| 7,178,555 B2 | 2/2007 | Engel et al. |
| 7,476,368 B2 | 1/2009 | Sargent et al. |
| 7,630,791 B2 | 12/2009 | Nguyen et al. |
| 7,993,602 B2 | 8/2011 | Moriyama et al. |
| 8,287,816 B2 | 10/2012 | Kral |
| 8,414,471 B2 | 4/2013 | Mandava et al. |
| 8,435,445 B2 | 5/2013 | Kral |
| 8,454,901 B1 | 6/2013 | Snyder, III |
| 8,733,551 B2 | 5/2014 | Parker et al. |
| 8,795,603 B2 | 8/2014 | Ghelman et al. |
| 8,851,287 B2 | 10/2014 | Becklin |
| 8,905,258 B2 | 12/2014 | Javid et al. |
| 9,348,013 B2 | 5/2016 | Rahim et al. |
| 9,703,264 B2 | 7/2017 | Freijsen et al. |
| 9,910,965 B2 | 3/2018 | Bufalini et al. |
| D818,841 S | 5/2018 | Newton |
| D819,409 S | 6/2018 | Newton |
| 10,405,938 B2 | 9/2019 | Ramsey |
| 10,418,831 B2 | 9/2019 | Racenet et al. |
| 10,456,494 B2 | 10/2019 | Roudebush et al. |
| 10,463,441 B2 | 11/2019 | Tate et al. |
| D909,883 S | 2/2021 | Newton |
| D921,490 S | 6/2021 | Newton |
| 11,445,900 B2 | 9/2022 | King et al. |
| 11,696,811 B2 | 7/2023 | Dalena et al. |
| 2003/0078472 A1 | 4/2003 | Parker |
| 2004/0101456 A1 | 5/2004 | Kuroshima et al. |
| 2005/0260097 A1 | 11/2005 | Williams et al. |
| 2006/0193761 A1 | 8/2006 | Moriyama et al. |
| 2007/0215507 A1 | 9/2007 | Glenn et al. |
| 2007/0228080 A1 | 10/2007 | Lin et al. |
| 2007/0286764 A1* | 12/2007 | Noguchi ............ A61B 1/00059 422/62 |
| 2008/0251102 A1 | 10/2008 | Haack et al. |
| 2009/0091453 A1 | 4/2009 | Ishida et al. |
| 2009/0104094 A1 | 4/2009 | Affaitati et al. |
| 2009/0123333 A1 | 5/2009 | Parker et al. |
| 2009/0206674 A1 | 8/2009 | Noguchi et al. |
| 2010/0176016 A1 | 7/2010 | Pell |
| 2010/0189598 A1 | 7/2010 | Fraundorfer |
| 2011/0002811 A1 | 1/2011 | Dane et al. |
| 2011/0192744 A1 | 8/2011 | Parker et al. |
| 2012/0152289 A1 | 6/2012 | Smith et al. |
| 2013/0019910 A1 | 1/2013 | Ledel |
| 2013/0105344 A1 | 5/2013 | Hartley |
| 2013/0192647 A1 | 8/2013 | Ledel et al. |
| 2014/0069841 A1 | 3/2014 | Pizzato et al. |
| 2014/0083886 A1 | 3/2014 | Winterrowd et al. |
| 2014/0182629 A1 | 7/2014 | Dromard et al. |
| 2014/0270583 A1 | 9/2014 | Anderson |
| 2014/0339114 A1 | 11/2014 | Griffin |
| 2014/0353203 A1 | 12/2014 | Hu et al. |
| 2015/0257632 A1 | 9/2015 | Ramsey |
| 2015/0259122 A1 | 9/2015 | Parker |
| 2015/0272680 A1 | 10/2015 | Suzuki |
| 2016/0058900 A1 | 3/2016 | Sato |
| 2016/0081540 A1 | 3/2016 | Suzuki |
| 2016/0095508 A1 | 4/2016 | Terliuc et al. |
| 2016/0249915 A1 | 9/2016 | Beckman et al. |
| 2017/0056122 A1 | 3/2017 | Ramsey |
| 2017/0091389 A1 | 3/2017 | Dukatz |
| 2017/0172397 A1 | 6/2017 | Zardini |
| 2018/0028703 A1 | 2/2018 | Mclaughlin et al. |
| 2018/0071045 A1 | 3/2018 | Cohen et al. |
| 2018/0134453 A1 | 5/2018 | Wassenburg |
| 2019/0021806 A1 | 1/2019 | Turbett |
| 2019/0183591 A1* | 6/2019 | Johnson ................ B25J 9/1666 |
| 2019/0365500 A1 | 12/2019 | Erdmann et al. |
| 2020/0118674 A1 | 4/2020 | Le et al. |
| 2020/0187767 A1 | 6/2020 | Kramer et al. |
| 2020/0205925 A1 | 7/2020 | Cummings et al. |
| 2020/0315731 A1 | 10/2020 | Zardini et al. |
| 2021/0076923 A1 | 3/2021 | Awau |
| 2021/0128768 A1 | 5/2021 | Jackson et al. |
| 2021/0138517 A1 | 5/2021 | Kakar et al. |
| 2021/0186641 A1 | 6/2021 | Cummings et al. |
| 2021/0187141 A1 | 6/2021 | Crotti |
| 2021/0212796 A1 | 7/2021 | Crotti |
| 2021/0356051 A1 | 11/2021 | Gray-Dreizler et al. |
| 2022/0211458 A1 | 7/2022 | Jackson et al. |
| 2022/0304560 A1 | 9/2022 | Jackson et al. |
| 2022/0304762 A1 | 9/2022 | Jackson et al. |
| 2022/0304764 A1 | 9/2022 | Jackson et al. |
| 2022/0387651 A1 | 12/2022 | Kendrick |
| 2022/0392102 A1 | 12/2022 | Ohara et al. |
| 2023/0082582 A1 | 3/2023 | Jackson et al. |
| 2023/0285614 A1 | 9/2023 | Kotani et al. |
| 2023/0285615 A1* | 9/2023 | Kotani .................... A61L 2/10 |

FOREIGN PATENT DOCUMENTS

| | | |
|---|---|---|
| DE | 202016105248 | 12/2016 |
| EP | 0091792 B1 | 1/1988 |
| EP | 0830295 A1 | 3/1998 |
| EP | 2689706 A2 | 1/2014 |
| EP | 2900117 A1 | 8/2015 |
| JP | 2007054343 | 3/2007 |
| JP | 2009172228 | 8/2009 |
| JP | 2008054861 | 3/2020 |
| WO | 9607364 | 3/1996 |
| WO | 2011151641 | 12/2011 |
| WO | 2018024690 | 2/2018 |

(56) References Cited

FOREIGN PATENT DOCUMENTS

| | | |
|---|---|---|
| WO | 2018/152400 | 8/2018 |
| WO | 2018152400 A1 | 8/2018 |

OTHER PUBLICATIONS

International Preliminary Report on Patentability dated Dec. 30, 2021, of International PCT Application No. PCT/US/2020/036618 dated Jun. 8, 2020.

International Search Report and Written Opinion of the International Searching Authority Dated Sep. 9, 2020, of International PCT Application No. PCT/US2020/036618 filed Jun. 8, 2020.

Steelco ED200 Endoscope Drying/Storage Cabinet' (Peacocks Medical Group) Jun. 20, 2018(Jun. 28, 2018) [retreived from the internet on Aug. 24, 2020 (Aug. 24, 2020) at htttps://web.archive.orglweb/20180620034054/https://www.peacocks.net/medical-decontamination/endoscopy/endoscopy-drying-cabinetsisteelco-ed200.

International Preliminary Report on Patentability dated Dec. 30, 2021, of International PCT Application No. PCT/US/2020/036630 dated Jun. 8, 2020.

International Preliminary Report on Patentability dated Dec. 30, 2021, of International PCT Application No. PCT/US/2020/036635 dated Jun. 8, 2020.

International Preliminary Report on Patentability dated Sep. 9, 2022 of International PCT Application No. PCT/US/2021/018463 dated Feb. 18, 2021.

International Preliminary Report on Patentability issued in PCT/US2020/019640, mailed Sep. 30, 2021.

International Search Report and Written Opinion mailed May 6, 2021, in International Application No. PCT/US2021/018463 filed Feb. 18, 2021.

International Search Report and Written Opinion mailed Nov. 20, 2020, in International Application No. PCT/US2020/036635 filed Jun. 8, 2020.

International Search Report and Written Opinion of the International Searching Authority Dated Jun. 5, 2020, of International PCT Application No. PCT/US2020/019640 filed Feb. 25, 2020.

International Search Report and Written Opinion of the International Searching Authority Dated Sep. 3, 2020, of International PCT Application No. PCT/US2020/036630 filed Jun. 8, 2020.

\* cited by examiner

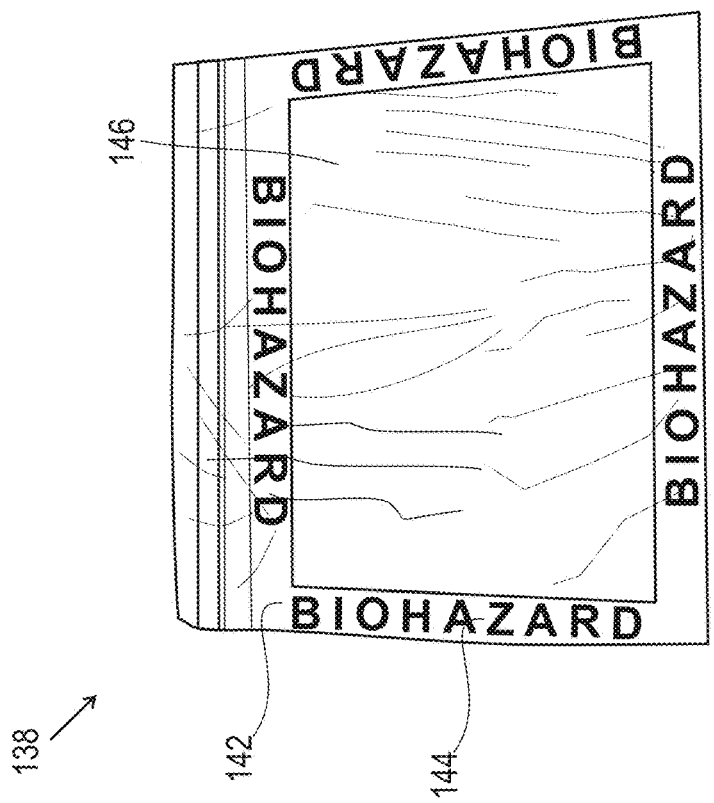
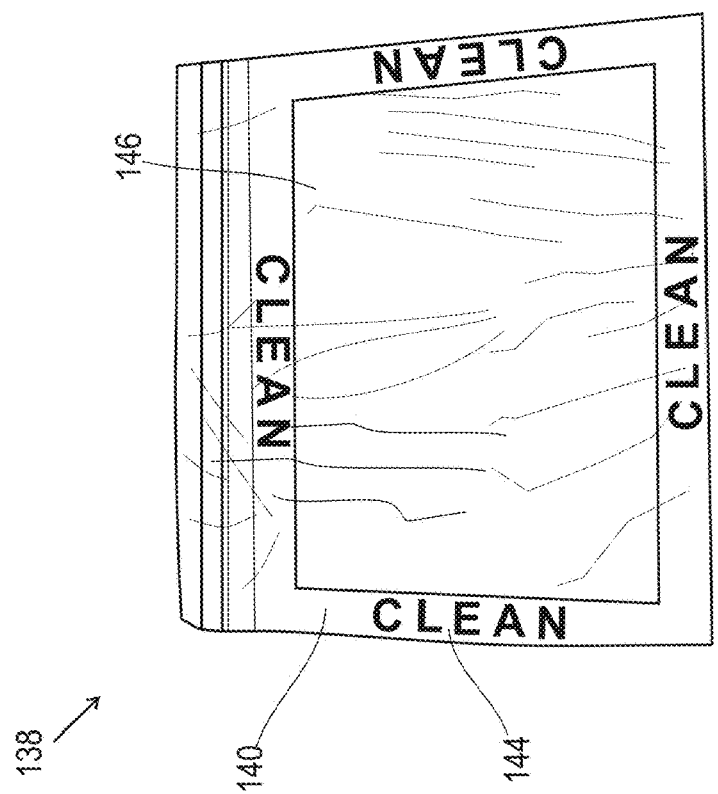
FIG. 18

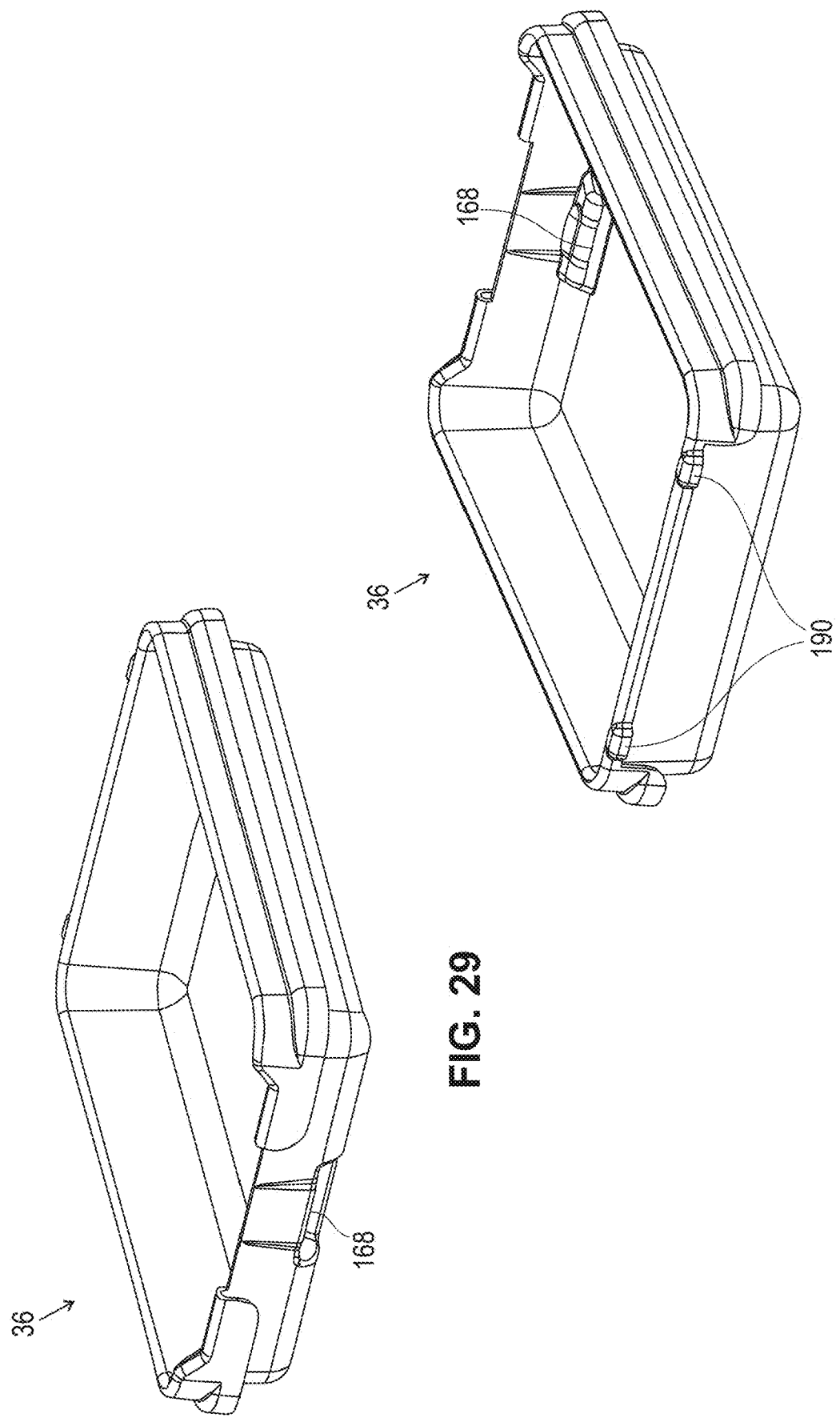

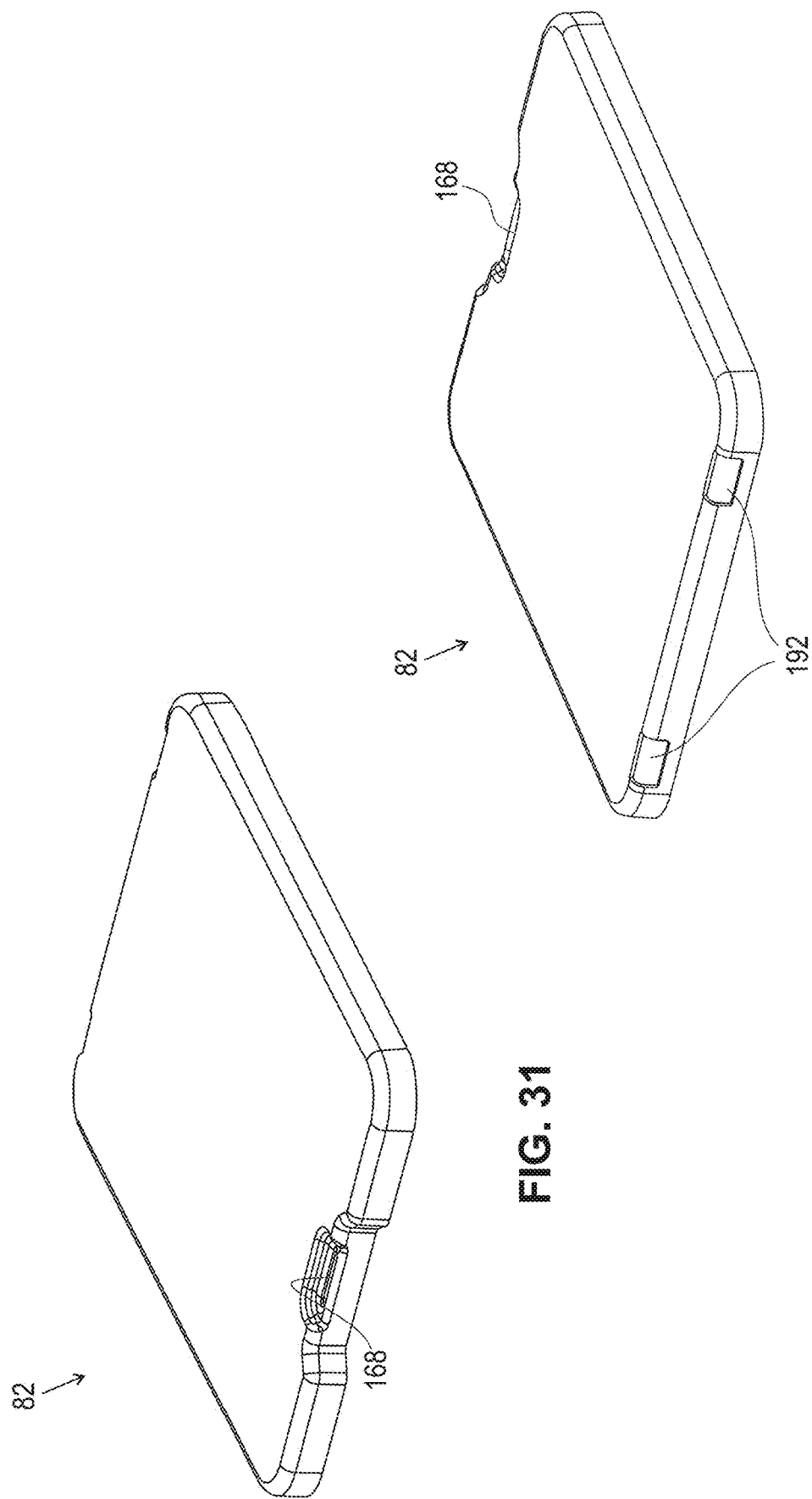

ENDOSCOPE STORAGE CART, SYSTEM AND METHODS

PRIORITY CLAIM

This application is a continuation of U.S. patent application Ser. No. 17/618,981 filed on Dec. 14, 2021, which is a 371 of and claims priority to and benefit of International Application with Serial No. PCT/US2020/36618 filed Jun. 8, 2020, which claims priority to and the benefit of U.S. Provisional application with Ser. No. 62/864,159, filed on Jun. 20, 2019, entitled ENDOSCOPE STORAGE CART, SYSTEM AND METHODS, which is herein incorporated by reference in its entirety.

BACKGROUND

Endoscopes are well-known in the art and are commonly used for numerous medical procedures. After each use, an endoscope will undergo reprocessing by cleaning, disinfection and/or sterilization to reduce or prevent contaminants from settling onto the endoscope, as well as to prevent the spread of diseases, viruses, bacteria, and illness.

After reprocessing, the endoscope is then stored in a clean environment. Under normal storage conditions, the degree of disinfection of the endoscope can be maintained at an acceptable level for a relatively short period. This short period of time can be as little as about 3 hours. This is due to the multiplication of residual pathogens which may remain on the endoscope after disinfection, or which may be present in the atmosphere. If the endoscope is not used in a further endoscopic procedure within this time, then further reprocessing may be necessary prior to its next use. Frequent and repeated reprocessing is undesirable, since it reduces the availability of the endoscope for endoscopic procedures, while increasing the operating costs, due to the need for cleaning and disinfectant materials and the operation of cleaning equipment. Furthermore, repeated reprocessing reduces the lifetime of the endoscope due to wear and tear.

The loss of High Level Disinfection Status (HLDS) over, for example, the 3 hour storage period is due to the inability of an Automated Endoscope Re-processor (AER) to completely dry the internal channels of the endoscope, due to the small internal diameter of these channels. The residual moisture within the channels provides an environment in which micro-organisms can quickly multiply.

When an endoscope is reprocessed, it is typically stored in a clean environment such as an endoscope storage cabinet or cart until it is used or reprocessed. However, these cabinets or carts do not easily indicate the time in which each endoscope has been reprocessed since most monitoring is done manually or make it easier to track the endoscope should contamination occur with that particular endoscope. Further, it can be easy for an endoscope to be removed from the cabinets or carts since there is no locking means built into the cabinets or carts, and endoscopes that are not safe for use can be removed.

Thus, there is a need to develop an endoscope storage cart that allows a user to identify the time a particular reprocessed endoscope has been placed in the cart and the time remaining prior to the endoscope needing reprocessing. There is also a need for an endoscope storage cart that can be locked and unlocked by an authorized user to prevent a contaminated endoscope from being used.

SUMMARY

New devices, systems and methods are provided for storing an endoscope that allows a user to identify the particular endoscope and the time the reprocessed endoscope has been placed in the cart and the time remaining before the endoscope requires reprocessing. In some embodiments, a cart for storage of an endoscope is provided. The cart comprises a housing having a slot configured to slidably receive a tray. The tray is configured to store an endoscope. A timer is coupled to the housing, slot and/or tray, that is configured to display increments of time that the endoscope is stored in the tray.

In some embodiments, a cart for storage of an endoscope is provided. The cart comprises a housing having a slot configured to slidably receive a tray. The tray is configured to store an endoscope. A timer is coupled to the housing, slot and/or tray that is configured to display increments of time that the endoscope is stored in the tray. A locking surface is disposed on the slot, the tray and/or the housing to lock the tray into the cart.

In some embodiments, a cart for storage of an endoscope is provided. The cart comprises a housing having a slot configured to slidably receive a tray. The tray is configured to store an endoscope. A timer is coupled to the housing, slot and/or tray and is configured to display increments of time that the endoscope is stored in the tray. A locking surface is disposed on the slot, the tray and/or the housing to lock the tray into the cart. A sensor is disposed in the slot or housing and is coupled to the timer that is configured to be activated when the tray is inserted into the slot.

In some embodiments, a cart for storage of an endoscope is provided. The cart comprising a housing having a runner assembly configured to receive a tray that is configured to store an endoscope. A timer is coupled to the housing, slot and/or tray, that is configured to display increments of time that the endoscope is stored in the tray.

In some embodiments, an endoscope storage system is provided. The system comprises a cart comprising a housing having a slot configured to slidably receive a disposable tray. The disposable tray configured to store an endoscope, and a timer coupled to the housing, slot and/or disposable tray. The timer is configured to display increments of time that the endoscope is stored in the disposable tray. A disposable liner and a disposable cover is provided. The disposable liner and the disposable cover configured to engage the disposable tray.

In some embodiments, a method for storing a reprocessed endoscope is provided. The method comprising placing a tray into an endoscope storage cart, the endoscope storage cart comprising a housing having a slot configured to slidably receive the tray, the tray for storing the reprocessed endoscope; and activating a timer coupled to the housing, slot and/or tray, the timer configured to display increments of time that the reprocessed endoscope is stored in the tray.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings.

FIG. 18 illustrates a perspective view of an embodiment of the cover of FIG. 16, where one side of the cover has the indicia clean labeled on it and the other side of the cover has the indicia biohazard labeled on it. The cover is configured to receive and enclose the entire tray.

FIG. 25A illustrates a perspective view of the locking surfaces of the tray and slot of FIG. 25 when the locking surfaces are matingly engaged and the tray is locked into the slot.

FIG. 25B illustrates a perspective view of the locking surfaces of the tray and slot of FIG. 25 when the locking surface of the slot disengages the mating surface of the tray to unlock the tray from the slot.

FIG. 29 illustrates a perspective front view of the tray of FIG. 27.

FIG. 30 illustrates a perspective back view of the tray of FIG. 27.

FIG. 31 illustrates a perspective front view of the rigid lid of FIG. 27.

FIG. 32 illustrates a perspective back view of the rigid lid of FIG. 27.

Figure 1:
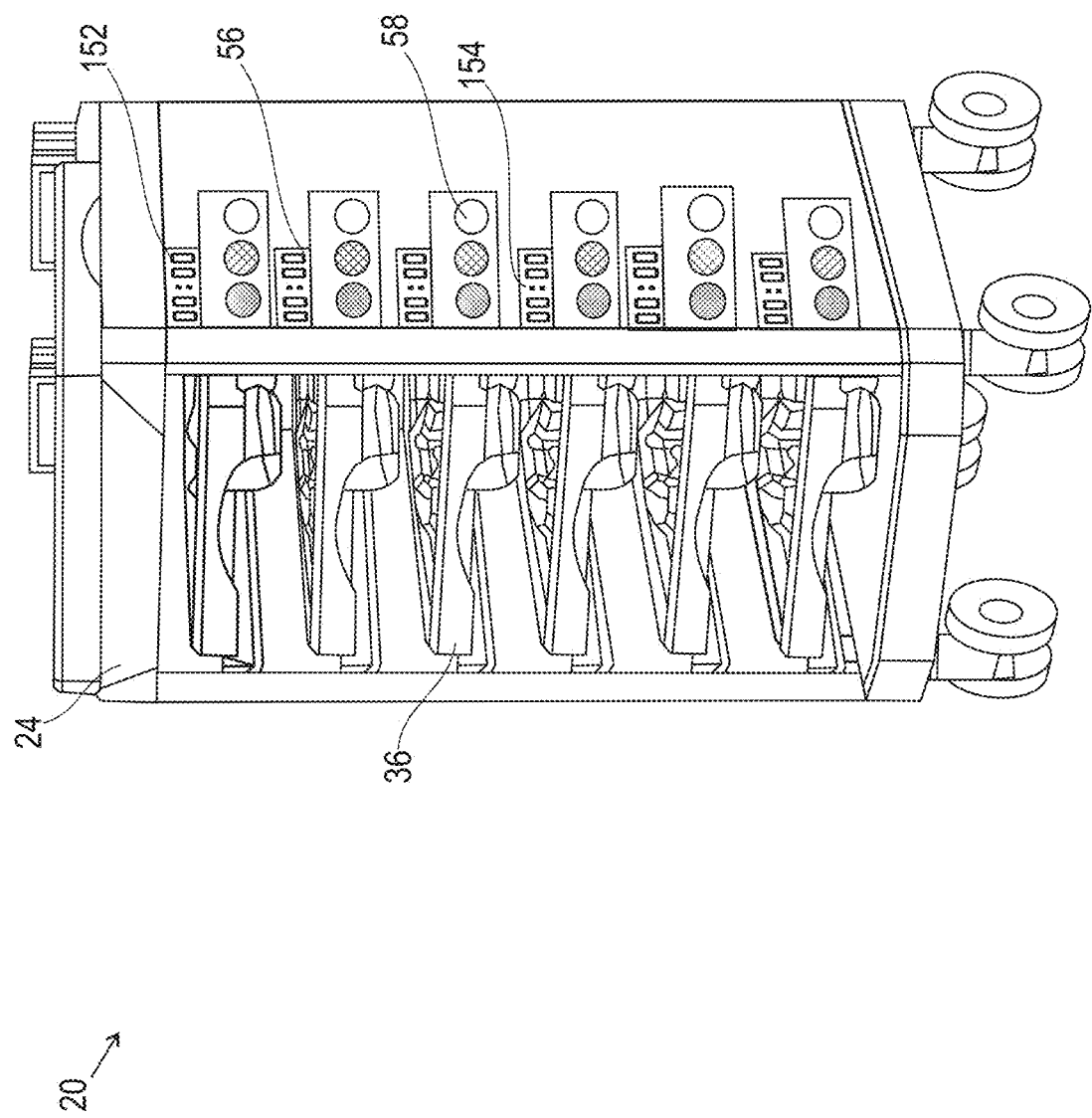
FIG. 1 illustrates a perspective view of a cart for storage of an endoscope. The cart comprises a housing having a slot configured to slidably receive a tray that is configured to store an endoscope. A timer is coupled to the housing that is configured to display increments of time that the endoscope is stored in the tray.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities, percentages or proportions of materials, conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "tray" includes one, two, three or more trays.

The term "High Level Disinfection Status" or "HLDS" refers to the destruction of all microorganisms with the exception of high levels of bacterial spores.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

In some embodiments, a storage system is provided that allows a user to identify the time a reprocessed endoscope has been reprocessed as well as the time remaining prior to an endoscope needing to be reprocessed again. In some embodiments, the system comprises a cart that uses different colored indicia such as lights to indicate different time increments. In some embodiments, the cart comprises an integrated locking system that can be activated when a pre-set time period has been reached in conjunction with indicia such as lights and a timer, indicating that the endoscope in no longer suitable for use on a patient and that it needs to be reprocessed. In some embodiments, the cart includes sensors that can indicate whether trays are full or empty in the cart and can initiate the timer to start.

In some embodiments, once a pre-set time period has been reached, the tray can be locked in position in the cart, and only an authorized user can deactivate the lock using for example, a pass key which can use for example, radiofrequency identification. In some embodiments, when an authorized user removes the tray, the cart can then reset and is ready for the next endoscope to be stored. In some embodiments, data can be collected by the cart to determine the number of endoscopes that are left in the cart for over a period of time, such as a three hour period of time. In some embodiments, data collected from the cart can be transmitted by WiFi or Bluetooth to a central monitoring area so that supervisory staff can see the status of all endoscopes in the reprocessing cycle.

Cart and Storage System

Figure 2:
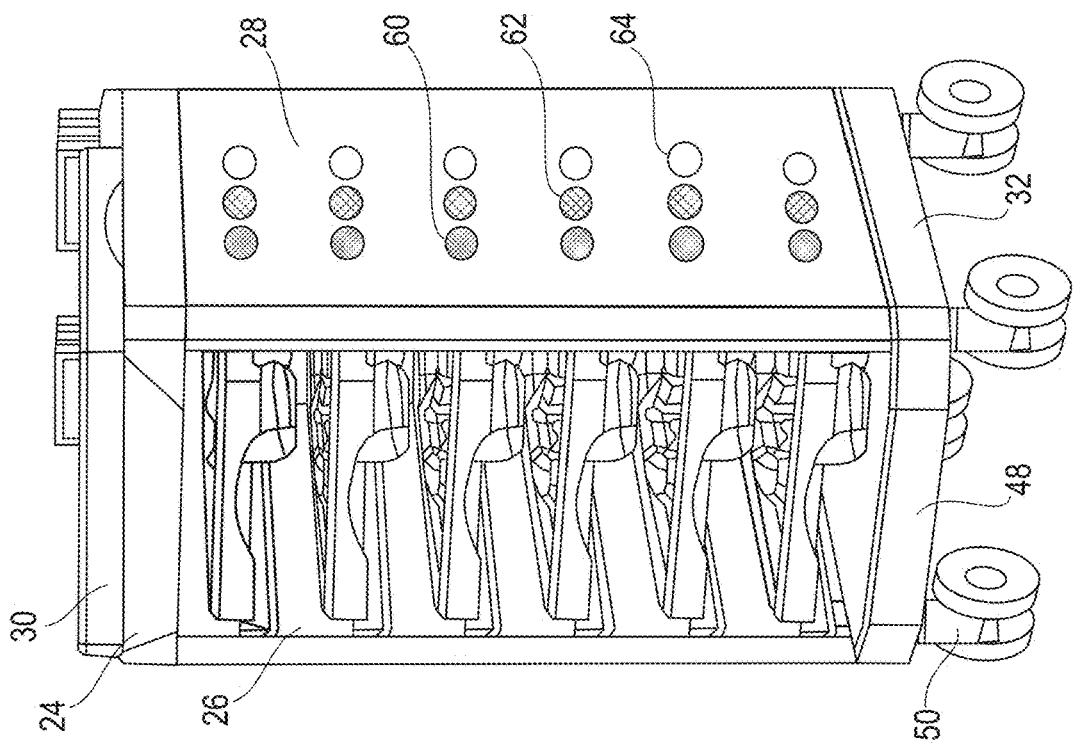
FIG. 2 illustrates a perspective view of the cart, shown in FIG. 1.
Figure 5:
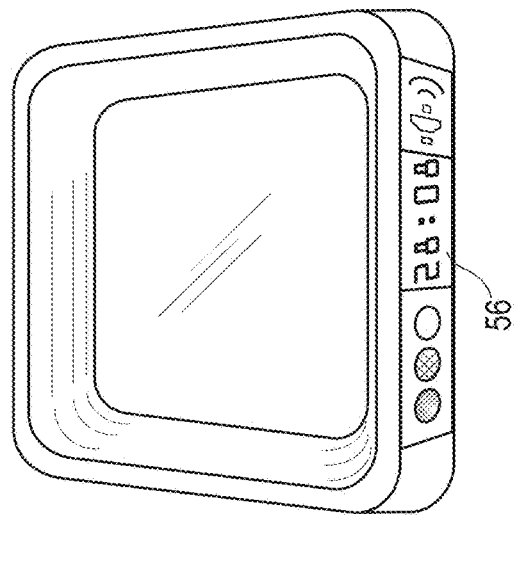
FIG. 5 illustrates a perspective view of a tray that is slidably received in the slot of the housing of the cart of FIG. 1. The tray is shown coupled with the timer.

Referring to FIGS. 1-37, a cart 20 is provided for storage of one or more reprocessed endoscopes 22, as shown in FIG. 1. The cart is configured to store and provide visual indication of the status of the endoscope and prevents the use of a contaminated endoscope for a procedure after a set period of time has expired. The cart comprises a housing 24. The housing includes opposing side walls 26, 28 and top and bottom walls 30, 32, as shown in FIG. 2. In some embodiments, the opposing side walls are longer in length than the top and bottom walls and the cart is in a rectangular configuration.

Figure 3:
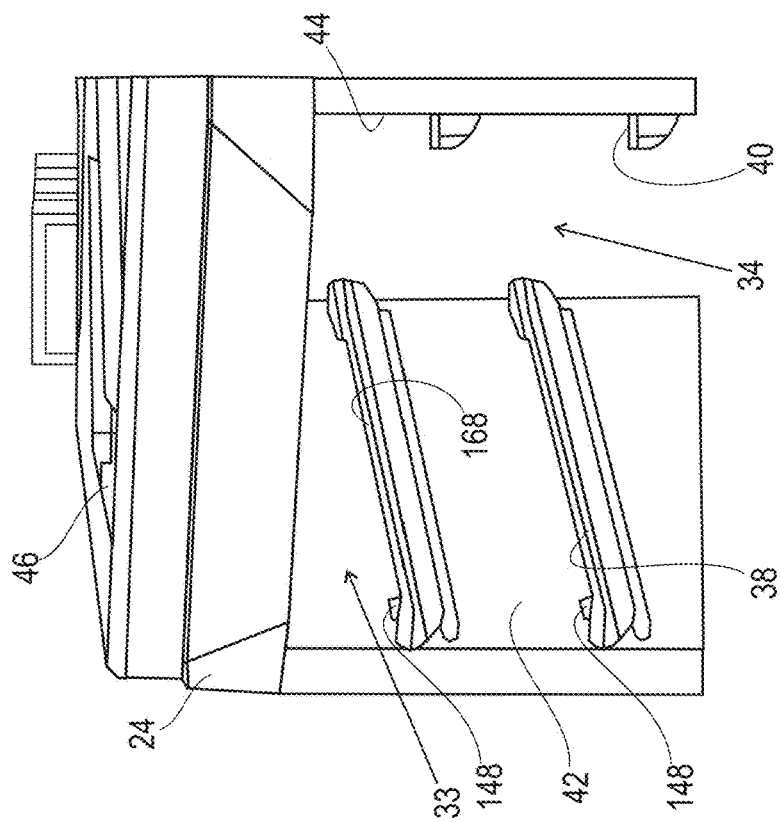
FIG. 3 illustrates a perspective view of a portion of the housing of the cart of FIG. 1.

The housing includes an interior 33 comprising one or a plurality of slots 34, each configured to slidably receive a tray 36, as shown in FIGS. 2 and 3. The slots are transverse relative to the opposing side walls. Each slot is defined by ledges 38, 40 that are in parallel orientation relative to each other. The ledges are each disposed on an inner surface 42, 44 of the opposing side walls. In some embodiments, the ledges are monolithic with the inner surfaces. In some embodiments, the ledges are attached to the inner surfaces and are not monolithic to the inner surfaces. In some embodiments, the cart can comprise 1 to about 12 slots for receiving 1 to about 12 trays. In some embodiments, the cart can comprise 1, 2, 3, 4, 5, 6, 7, 8, 9, 10, 11 to about 12 slots and 1, 2, 3, 4, 5, 6, 7, 8, 9, 10, 11 to about 12 trays.

In some embodiments, the top wall can include an exterior surface 46 configured for resting a tray and/or other instruments before or after the tray is inserted into a slot for storage, as shown in FIG. 3. In some embodiments, the exterior surface can be downwardly dished or flat so that the tray and/or other instruments can rest on the exterior surface of the top wall of the cart.

Figure 4:
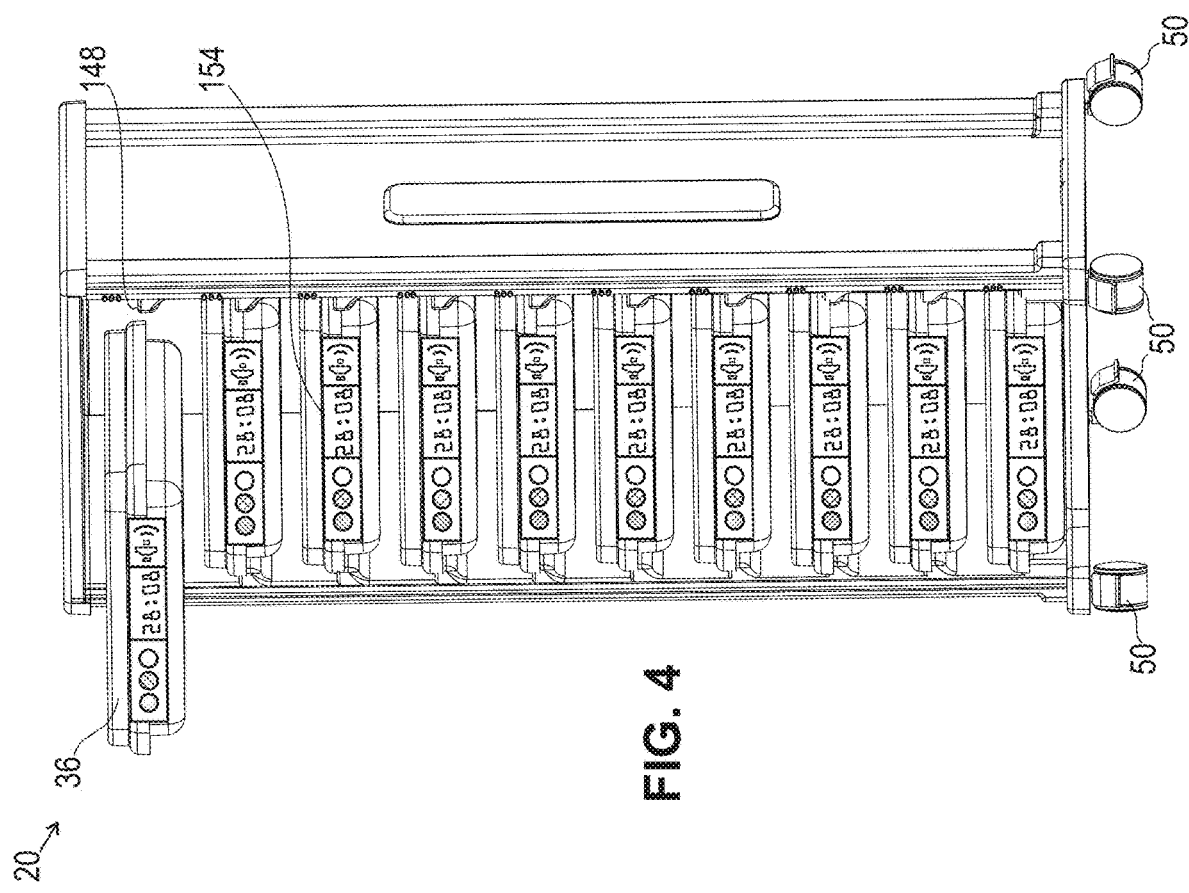
FIG. 4 illustrates a perspective view the cart of FIG. 1 where the timer is coupled to the front of tray.
Figure 36:
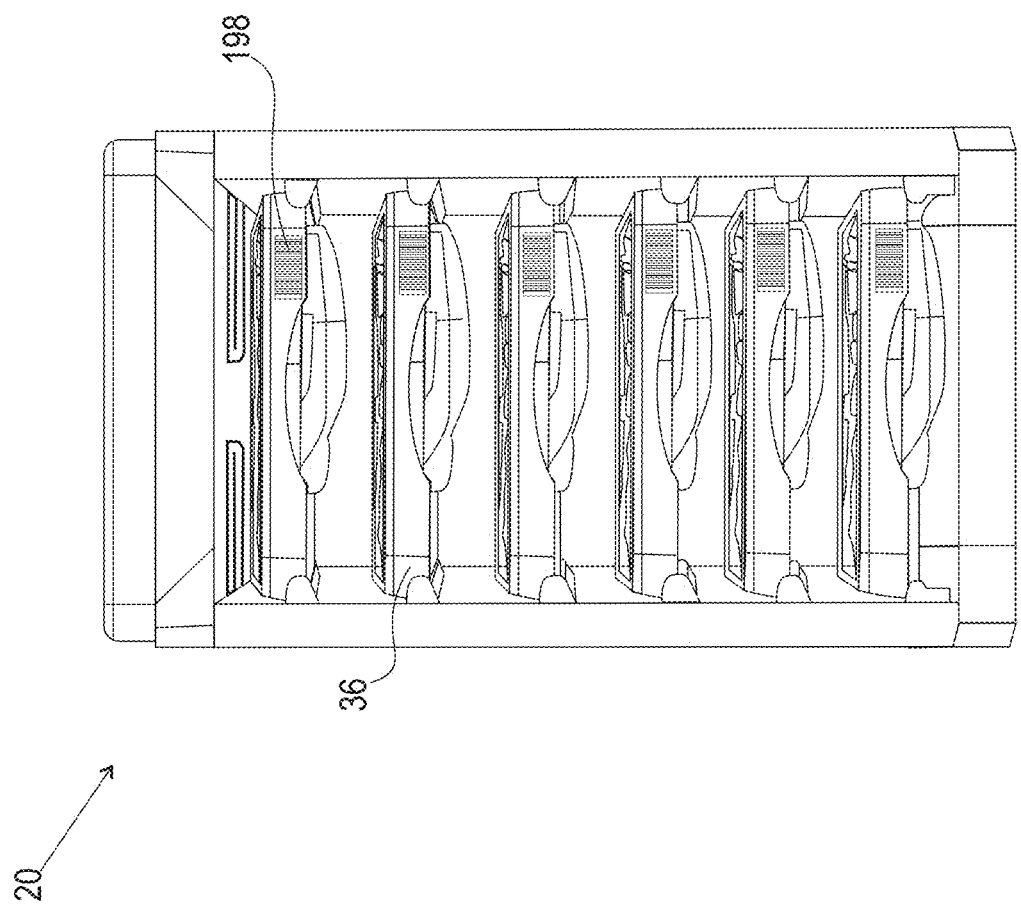
FIG. 36 illustrates a front view of an embodiment of the cart of FIG. 1 where the tray includes a barcode and the cart includes a wireless barcode reader so that the tray can be tracked.

In some embodiments, the bottom wall includes an exterior surface 48 that attaches to a plurality of wheels 50, such as caster wheels. In some embodiments, the cart can include 4 or more wheels disposed at corners of the exterior surface, as shown in FIGS. 1, 2 and 4. In some embodiments, the cart does not include wheels and is stationary, as shown in FIG. 36.

Figure 6:
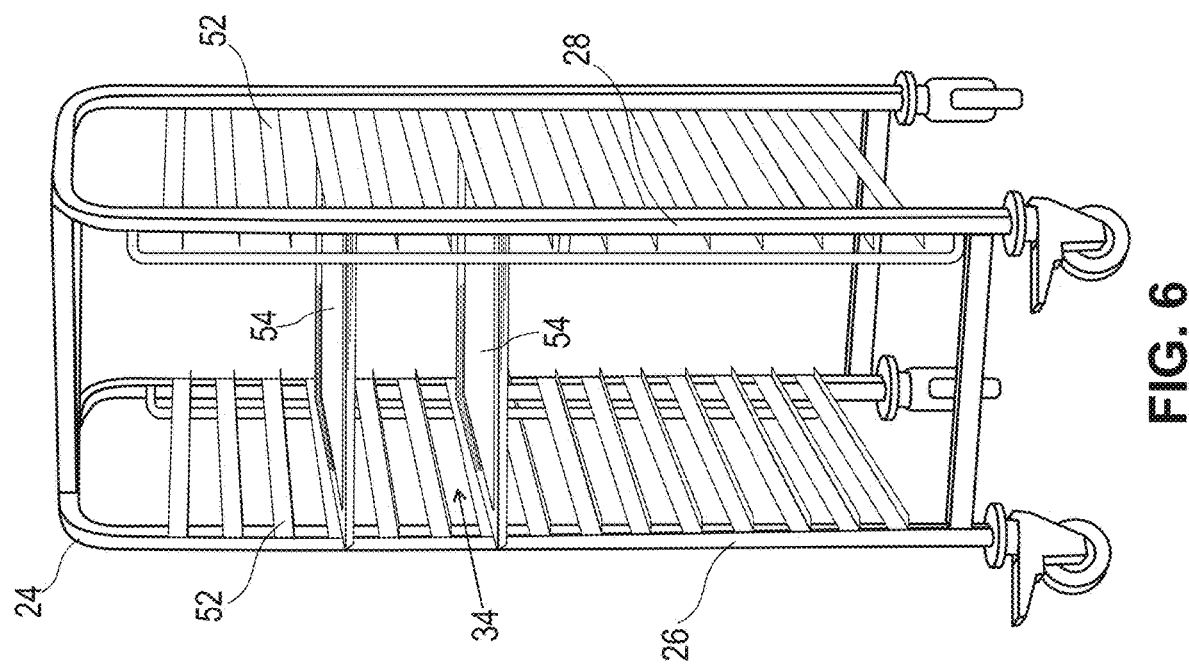
FIG. 6 illustrates a perspective view of an embodiment of the cart of the current application.

As shown in FIG. 6, in some embodiments, the cart can alternatively include transverse strips 52 that define side walls 26, 28. In this embodiment, a board 54 can be suspended from the strips and the tray can engage the board and the strips to fit securely into the cart. In this embodiment, the cart can be washed as well as the tray so that they can be reusable and repeatedly disinfected. In some embodiments, a cabinet can alternatively be used instead of the cart.

The cart includes a timer 56 coupled to the housing. In some embodiments, the timer can be coupled to the slot and/or the tray. The timer is configured to display increments of time that the endoscope is stored in the tray. In some embodiments, the timer is paired with indicia 58 comprising numbers, letters, colors, audible sounds, symbols and/or lights to indicate the increments of time that the endoscope is stored in the tray and endoscope status, as shown in FIGS. 1, 2 and 4.

In some embodiments, the indicia comprise a first light 60, a second light 62, and a third light 64, as shown in FIG. 2. In some embodiments, the first light is a green light that indicates a reprocessed endoscope at a time increment, the second light is an amber light that indicates the reprocessed endoscope at a time increment, and the third light is a red light that indicates that the endoscope needs to be reprocessed after a time increment.

The increments of time/time increment can be any increment, for example, from about 1 minute to about 72 hours. In some embodiments, the increments of time/time increment can be from about 1 minute, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 minutes, 1 hour, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 to about 72 hours. In some embodiments, the increments of time/time increment can be selected to correspond with the HLDS of the endoscopes. For example, the increments of time can be from about 0.5 to about 3 hours. In some embodiments, the HLDS is based on national or local guidelines.

In some embodiments, the timer is electrically coupled to the housing, slot, and/or the tray, as shown in FIGS. 1, 2, 4 and 5 and as described herein. In some embodiments, the timer is manually activated. For example, the timer can be activated by pressing a button to start the time sequence.

Figure 8A:
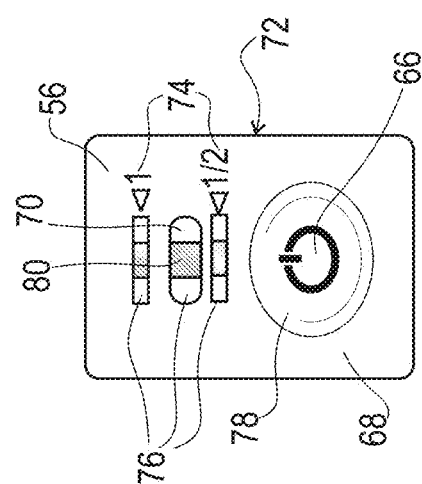
FIG. 8A illustrates a front view of the chemical time strip shown in FIG. 8.
Figure 8:
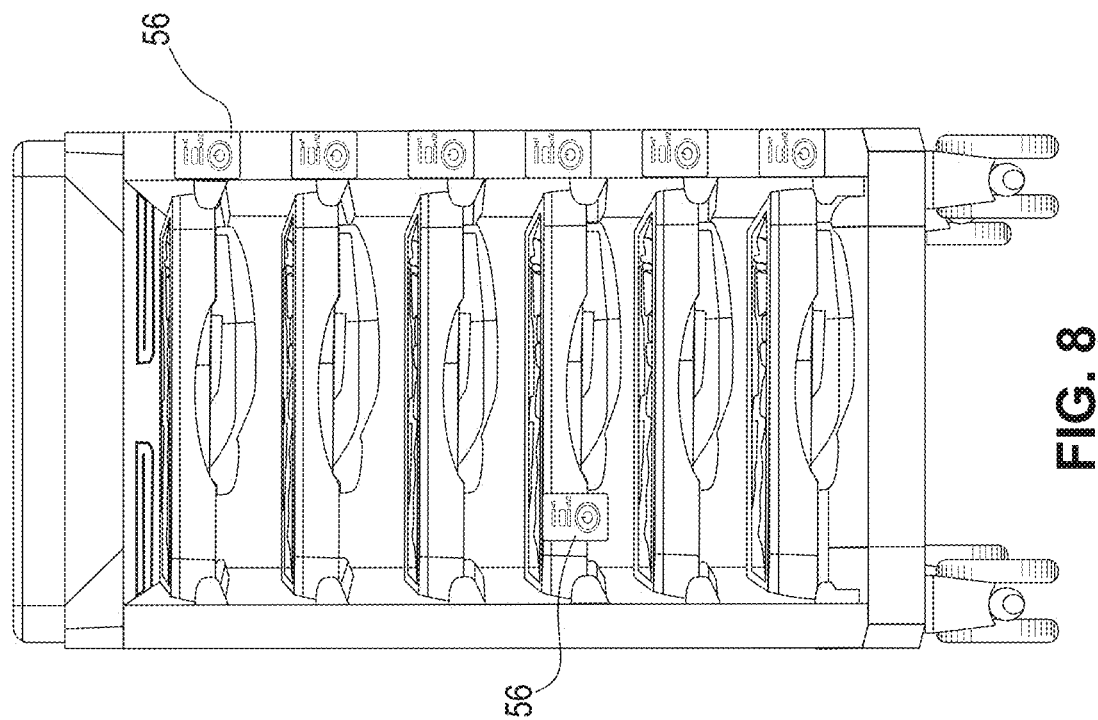
FIG. 8 illustrates a front view of an embodiment of the cart of FIG. 1 where the timer is a chemical time strip.
Figure 9:
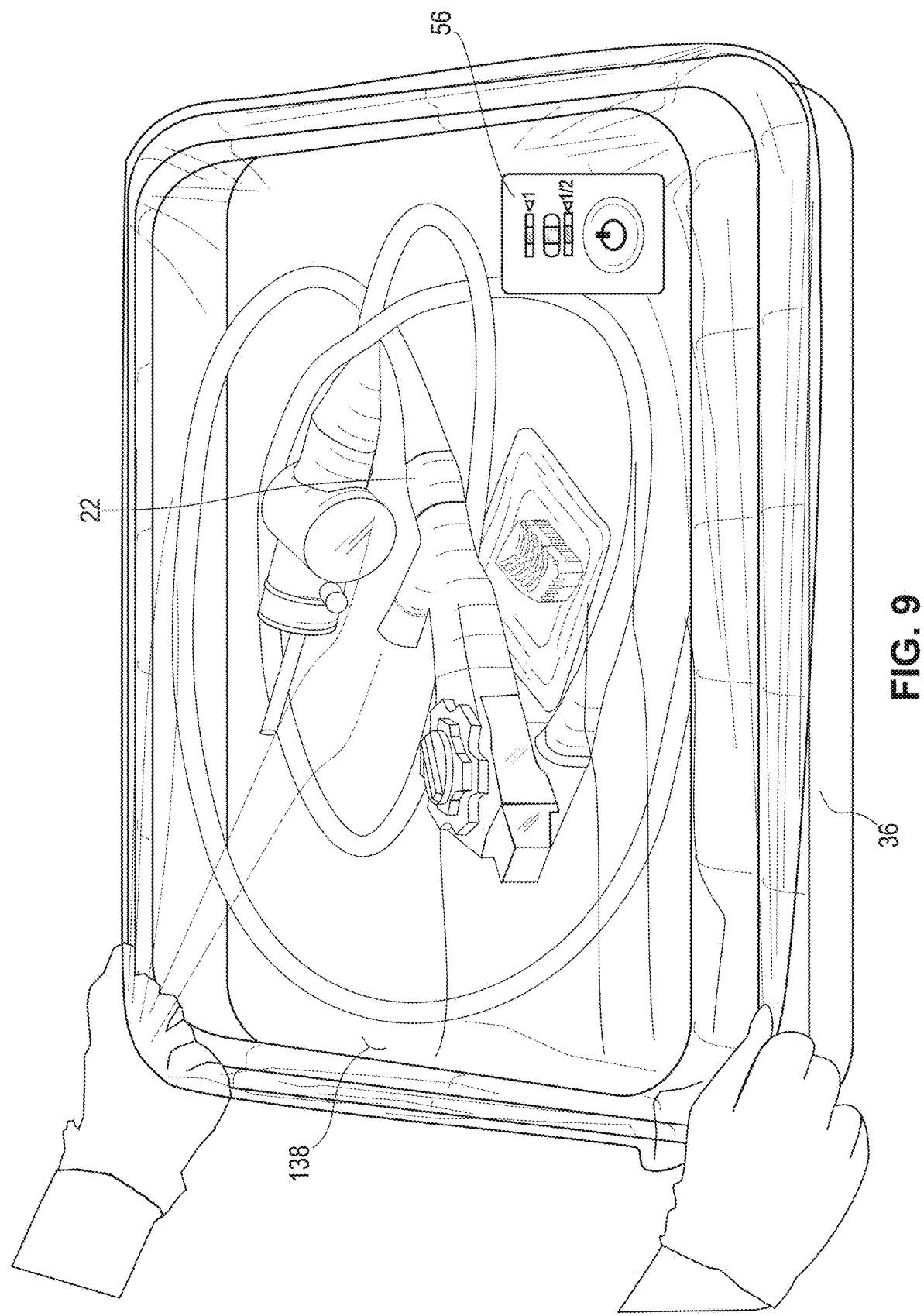
FIG. 9 illustrates a perspective view of the chemical time strip of FIG. 8 disposed with a cover that is engageable with the tray.

In the embodiments shown in FIGS. 8, 8A and 9, the timer can be a chemical strip that is manually activated by a user. In some embodiments, the chemical strip can have an activation button 66, as shown in FIG. 8A. The activation button can be manually pressed by a user to activate the strip. The strip includes a first outer layer 68, a second intermediate layer 70 and a third backing layer 72. The first outer layer includes the activation button, a time increment marker 74 and viewing windows 76 to visually indicate to a user the period of time since activation of the chemical strip has occurred. The second intermediate layer can be made from a porous membrane material for which a chemical and/or fluid located inside of the strip travels through. Pressing the activation button releases the chemical and/or the liquid from a blister 78. A colored line 80 will appear after the activation button is pressed to confirm that the chemical strip is active. As time passes, the colored line will progress and when the viewing windows are completely filled, the full time period has elapsed. On inspection of the timer, there are indicia that the shelf life of the reprocessed endoscope in that particular tray is acceptable, approaching the expiration time, or the time has expired in which the reprocessed endoscope should not be used, where it can be removed to be reprocessed and/or cleaned. The user simply removes the endoscope and/or drawer containing the endoscope when time is expired. In this way a HLDS quality for the endoscope can be ensured.

In some embodiments, a suitable chemical strip that can be used in the current application to monitor time is available from Timestrip UK Ltd, of Sheraton House, Castle Park, Cambridge, CB3 0AX, United Kingdom as Timestrip® 1 hour or Timestrip® 12 hours.

In some embodiments, the chemical strip is attached to the housing, slot and/or the tray by an adhesive that is attached to the back of the third backing layer. In some embodiments, the adhesive can be a pressure sensitive adhesive and/or a removable adhesive. In some embodiments, the adhesive can be manufactured from a glue, rubber, acrylic, and/or an epoxy.

Figure 7:
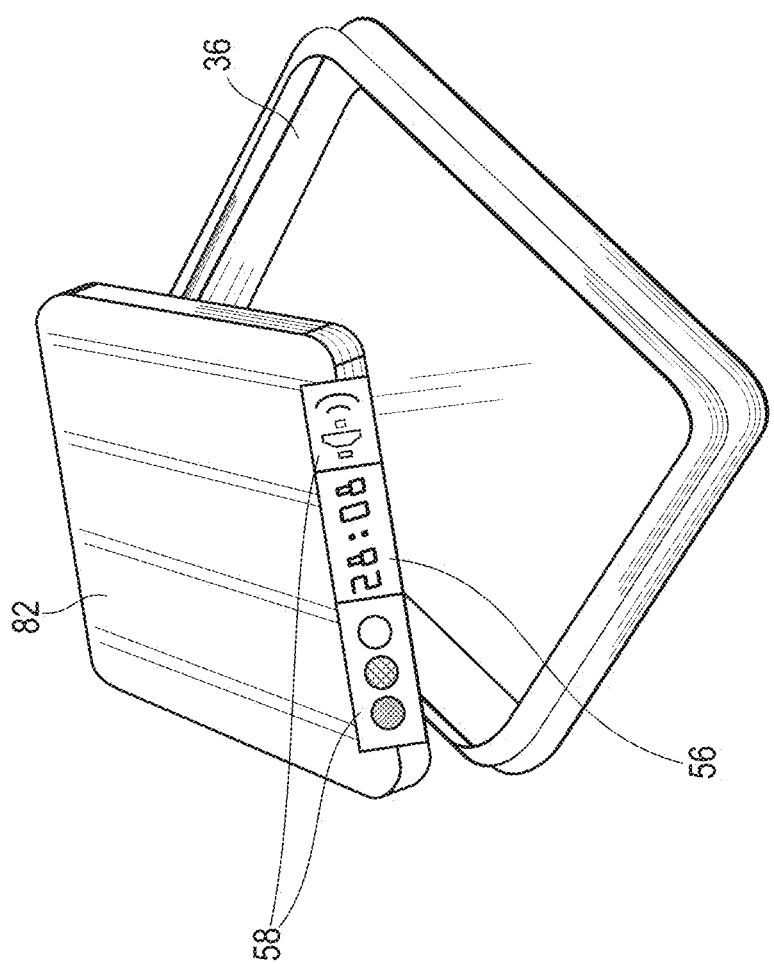
FIG. 7 illustrates a perspective view of a tray with a rigid lid. The rigid lid is shown coupled with the timer.

The timer can be attached to the housing, slot and/or tray and can be activated when the tray is inserted into the slot, as described herein. In some embodiments, the timer can also be coupled to a rigid lid 82 that engages with the tray, as shown in FIG. 7.

Figure 10:
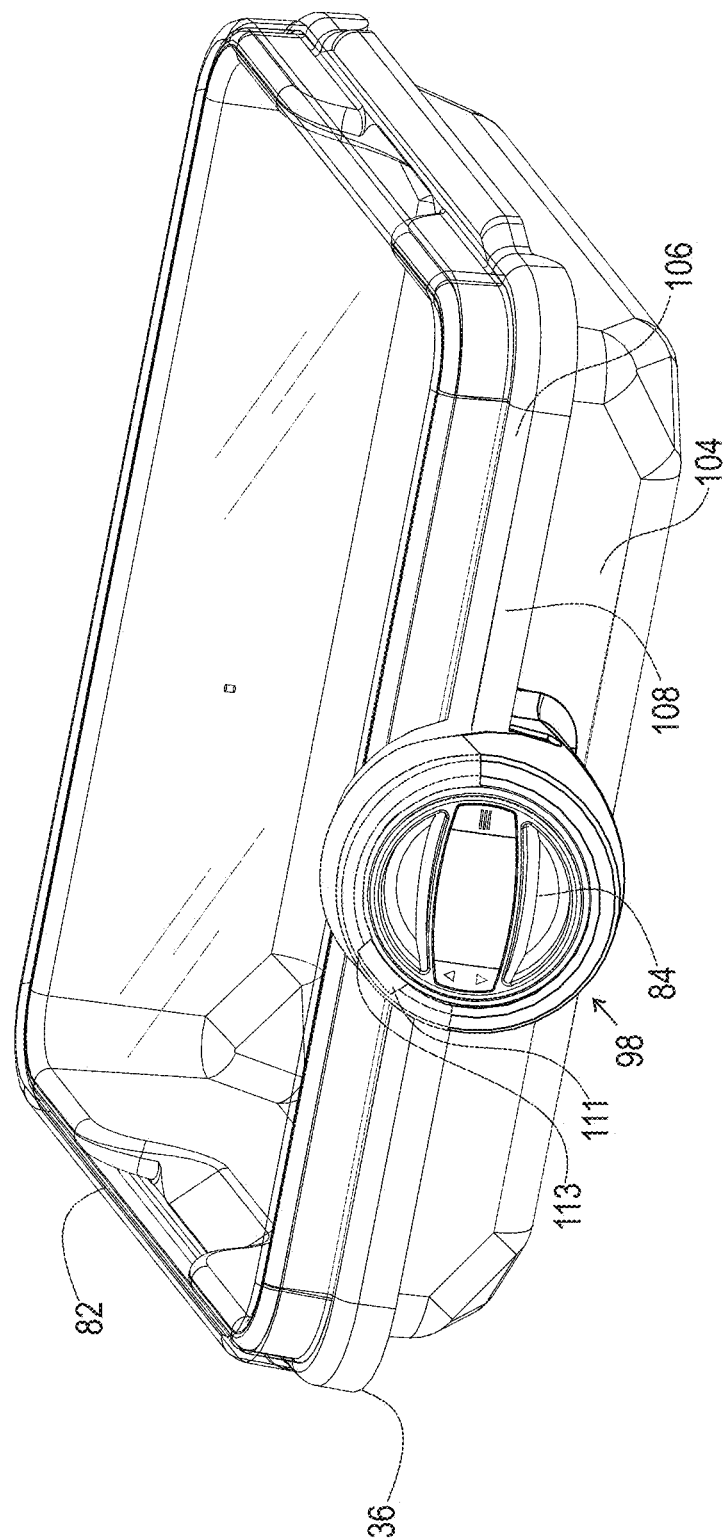
FIG. 10 illustrates a perspective view of an embodiment of the tray and an embodiment of the rigid lid where the timer is a digital timer that is removable from the tray and the lid.
Figure 11C:
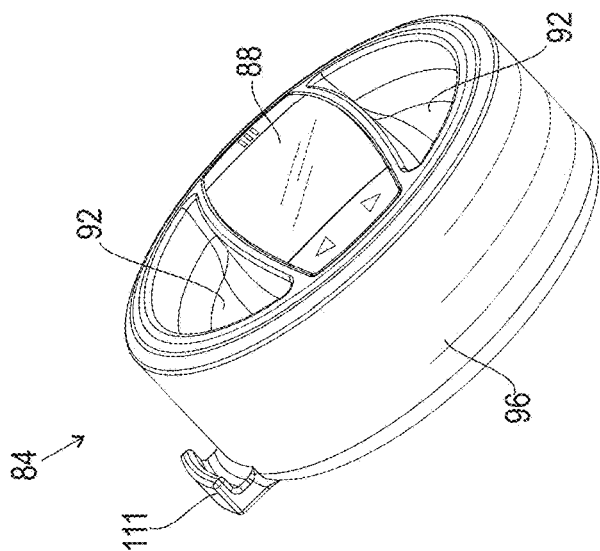
FIG. 11C illustrates a perspective view of the digital timer of FIG. 10.
Figure 11B:
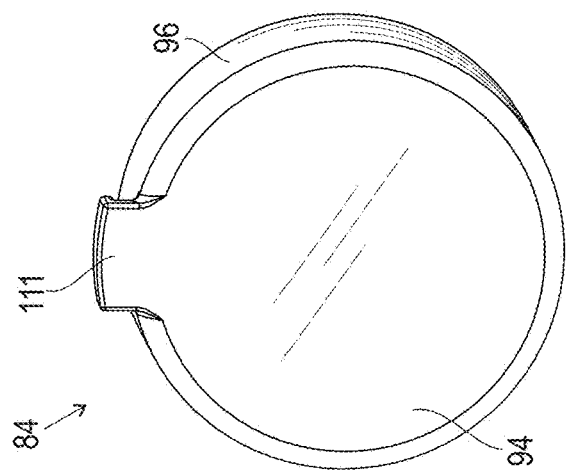
FIG. 11B illustrates a back view of the digital timer of FIG. 10.
Figure 11A:
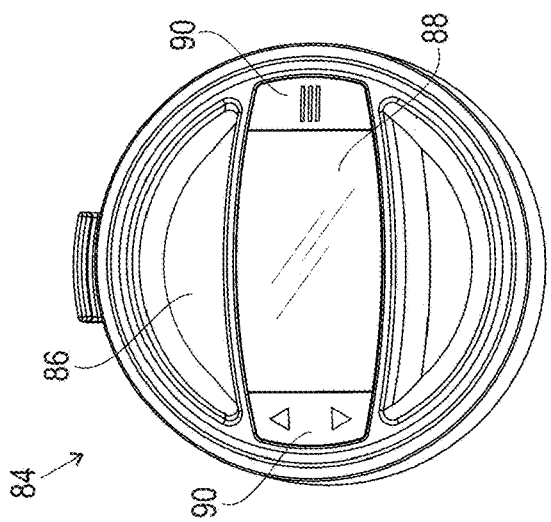
FIG. 11A illustrates a front view of the digital timer of FIG. 10.
Figure 12:
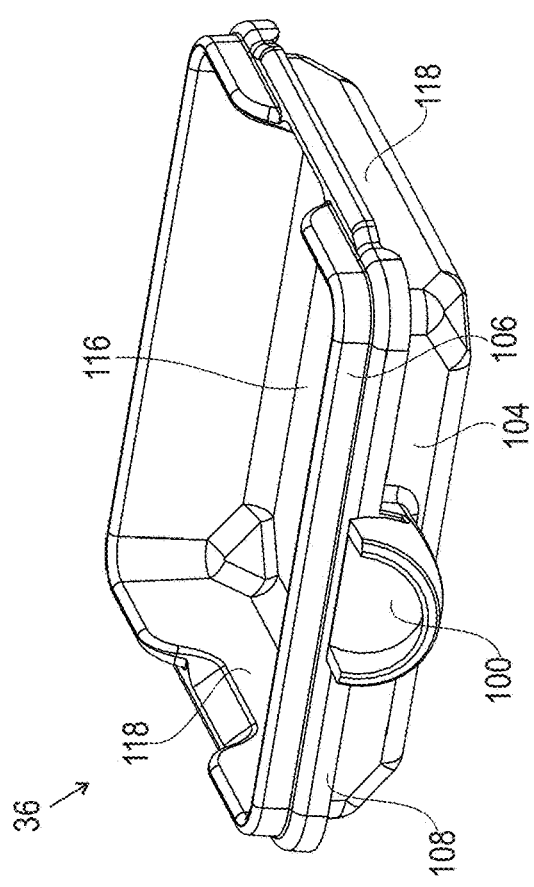
FIG. 12 illustrates a perspective front view of the tray of FIG. 10.
Figure 14:
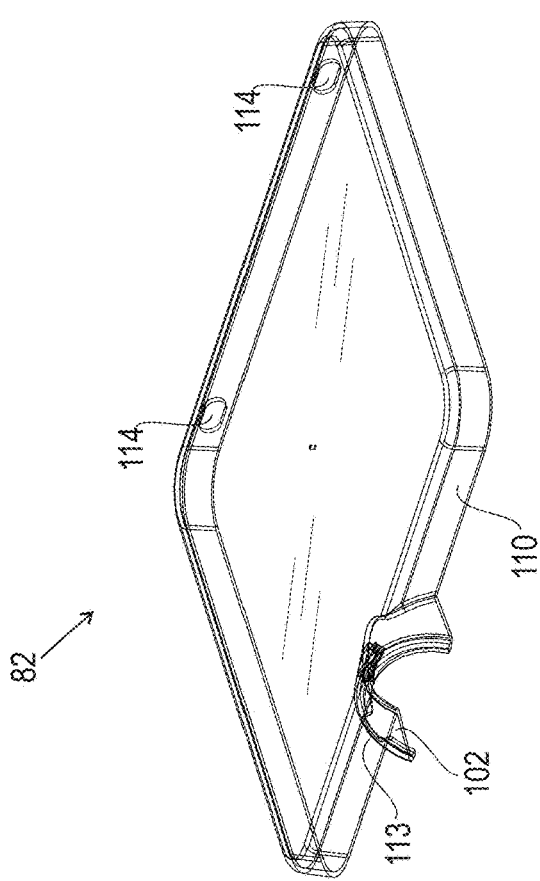
FIG. 14 illustrates a perspective view of the rigid lid of FIG. 10.
Figure 15:
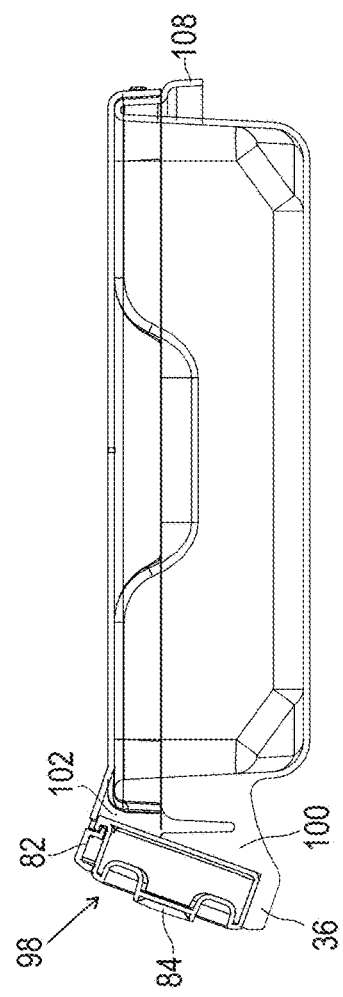
FIG. 15 illustrates a cross sectional side view of the digital timer engaged with the tray and rigid lid of FIG. 10.

In some embodiments, the timer is electronic and/or digital, such as digital timer 84, shown in FIGS. 10-11C and 15. The digital timer is configured to be removable from the rigid lid and/or the tray and can be rechargeable. The digital timer includes a front face 86 that includes a display 88 that visually indicates the amount of time that the endoscope is stored in the tray. Buttons 90 are located adjacent to the display which are used to set the digital timer for use. Portions 92 of the front face of the digital timer can be recessed, as shown in FIG. 11C to assist in gripping and/or handling the digital timer. As shown in FIG. 11B, a back surface 94 and a circumferential wall 96 of the digital timer are configured to engage with a circumferential recess 98 that is formed from a portion 100 of the tray and a portion 102 of the rigid lid. For example, the portion of the tray can be defined from a section of an exterior sidewall 104 of the tray, a rim 106 and/or a lip portion 108 of the tray, as shown in FIGS. 10, 12 and 15. The portion of the rigid lid can be defined from a rim 110 of the rigid lid, as shown in FIG. 14. A tab 111, as shown in FIGS. 11B and 11C is formed from the back surface of the digital timer and is configured for locked engagement with an indent 113 formed within portion 102 of the rigid lid, as shown in FIG. 14.

Figure 13:
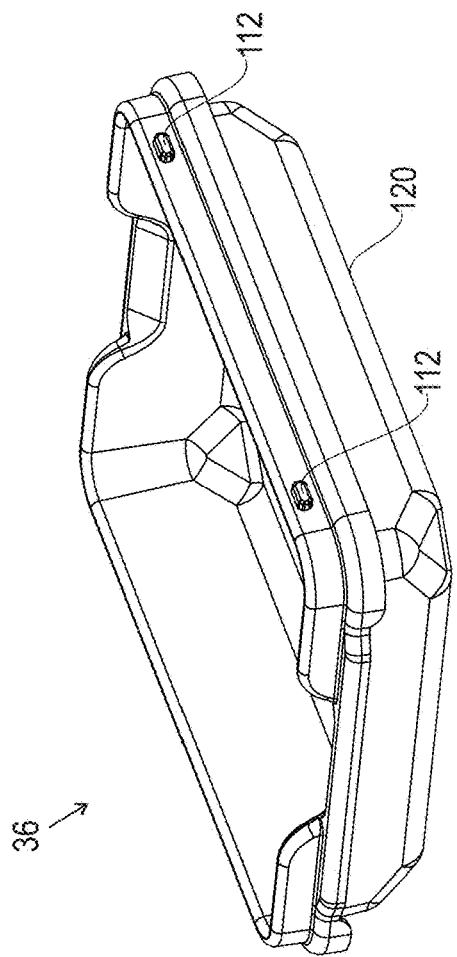
FIG. 13 illustrates a perspective back view of the tray of FIG. 10.

The rigid lid can removably engage with the tray, as shown in FIGS. 10, 13, 14 and 15. As shown in FIGS. 13 and 14, the tray can include projections 112, for example 2 projections that are located on the rim of the tray that correspond with recesses 114, for example 2 recesses that are located on the rim of the rigid lid. A user can engage the rigid lid with the tray by inserting the projections of the tray into the recesses of the rigid lid.

Figure 16:
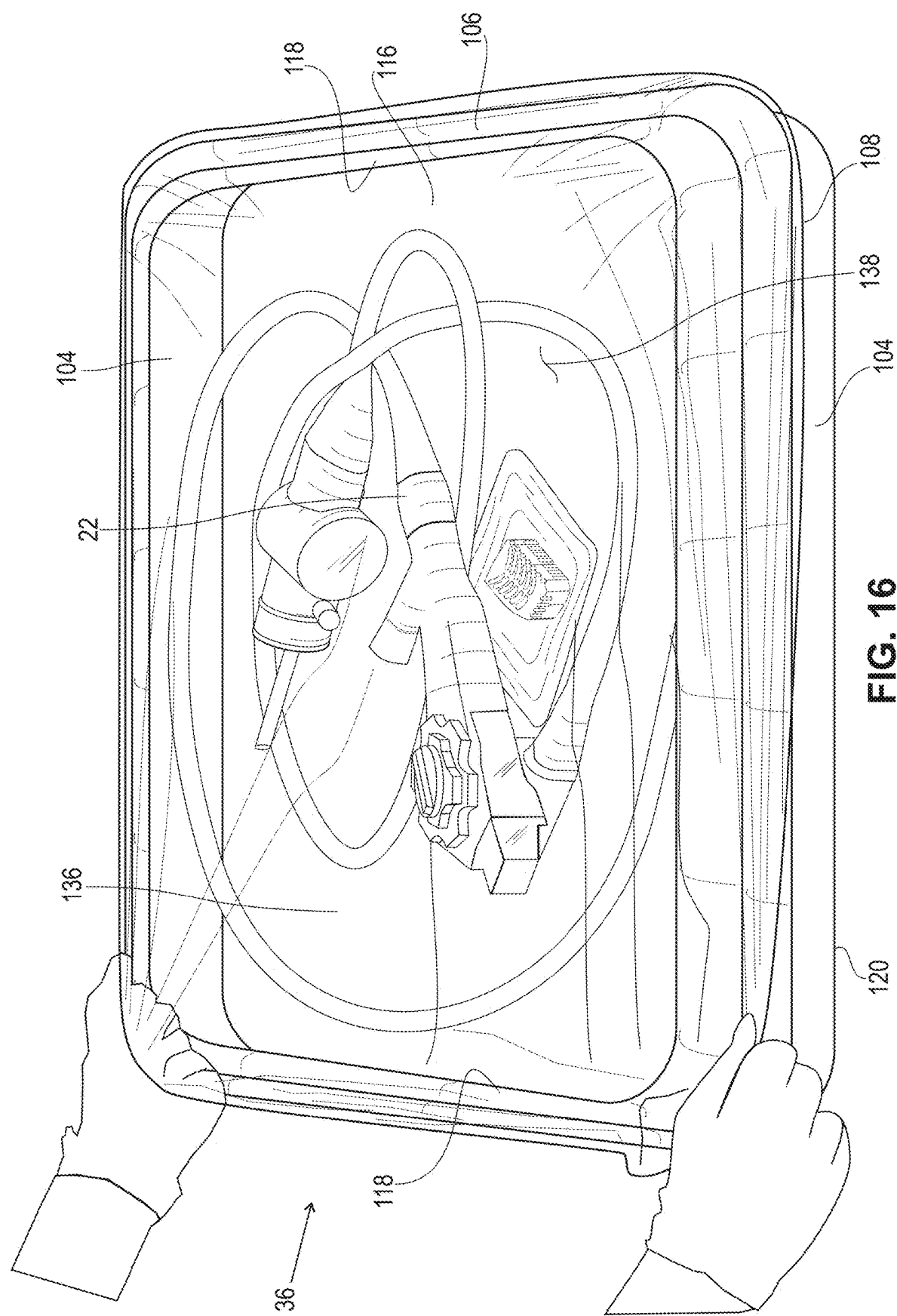
FIG. 16 illustrates a perspective view of the tray of FIG. 5. The tray is engaged by a disposable liner and a disposable cover, and an endoscope is shown disposed within the tray.
Figure 17:
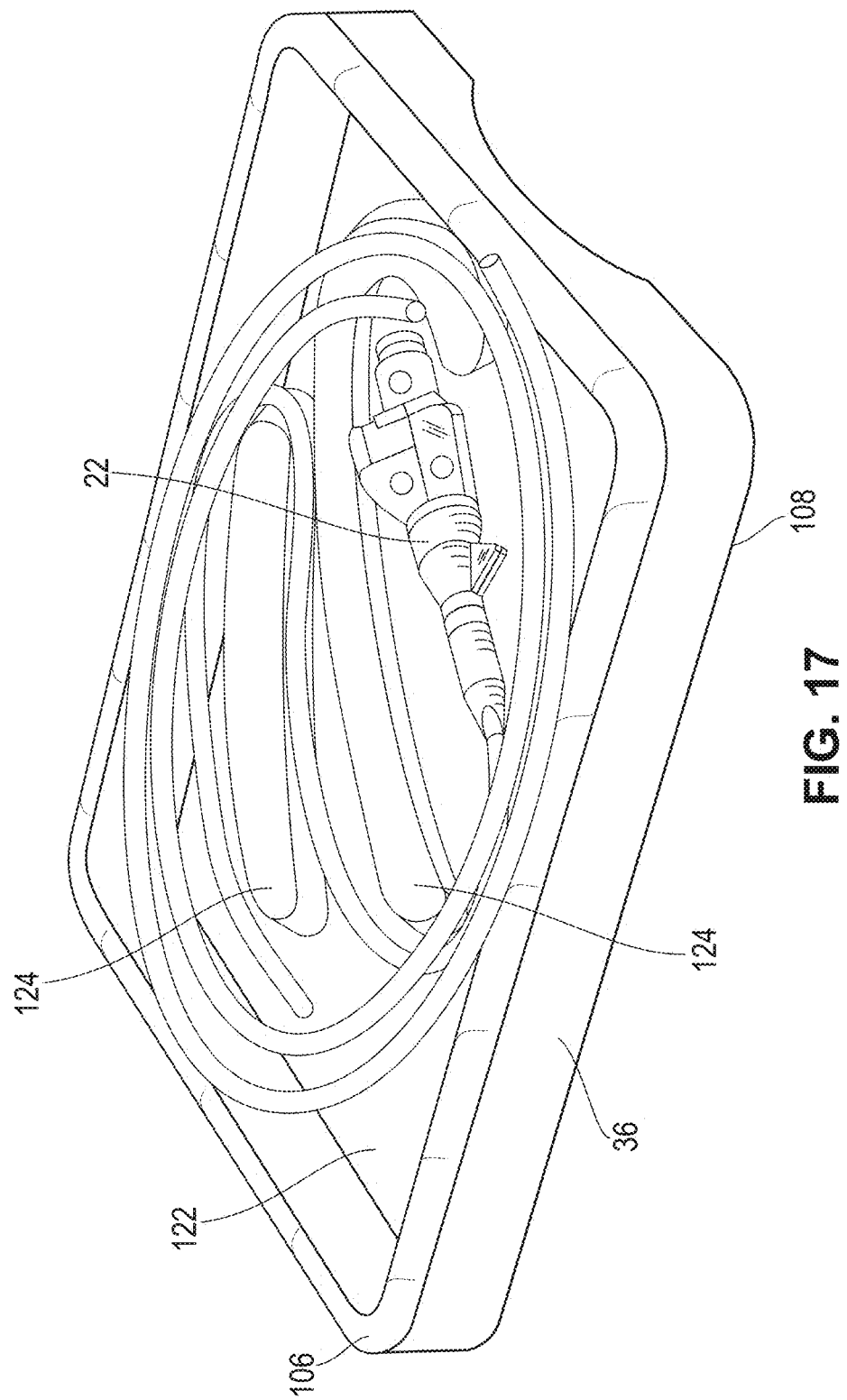
FIG. 17 illustrates a perspective view of an embodiment of the tray of FIG. 5 comprising upstanding elements to store and protect the endoscope.

As described above, tray 36 is configured to be slidably received in the slot of the cart. The tray is also configured to store reprocessed endoscope 22, as shown in FIGS. 16 and 17, which can be obtained from automated endoscope reprocessors manufactured by, for example, Medivators Inc., Minneapolis, MN, USA. In some embodiments, the tray is a reusable tray and can be rigid. In some embodiments, the tray is similar to the tray described in U.S. Pat. No. 6,749,063, assigned to Cantel (UK) Limited. This patent is incorporated herein by reference.

The tray includes an interior compartment 116, the exterior sidewalls 104, opposing end walls 118, and the rim that is curled over to form the lip portion. A bottom surface 120 of the tray contacts the exterior side walls and the end walls, as shown in FIG. 16.

In some embodiments, the interior compartment of the tray comprises a planar base 122 and surrounding upstanding elements such as walls 124, as shown in FIG. 17, to store and protect the endoscope. In some embodiments, the entire tray base can be planar or portions of the tray can be planar, while other portions of the tray can be non-planar or arched, defining walls 124. In some embodiments, the tray does not have a lip.

In some embodiments, dimensions of the tray must be sufficient to accommodate substantially all sizes of flexible medical endoscopes in a coiled state without undue stress being applied to the flexible portions of the endoscope. However, the tray can also be sufficiently small to permit it to be easily carried by a person. In some embodiments, the tray is constructed and dimensioned to provide support for the endoscope coiled in a stress-free state.

In some embodiments, the tray is rigid and re-usable and comprises a base having planar and non-planar portions and surrounding sidewalls upstanding therefrom, the tray being formed of a semi-rigid material capable of withstanding repeated disinfection and dimensioned to provide support for a flexible medical endoscope coiled in a stress-free state.

Figure 19:
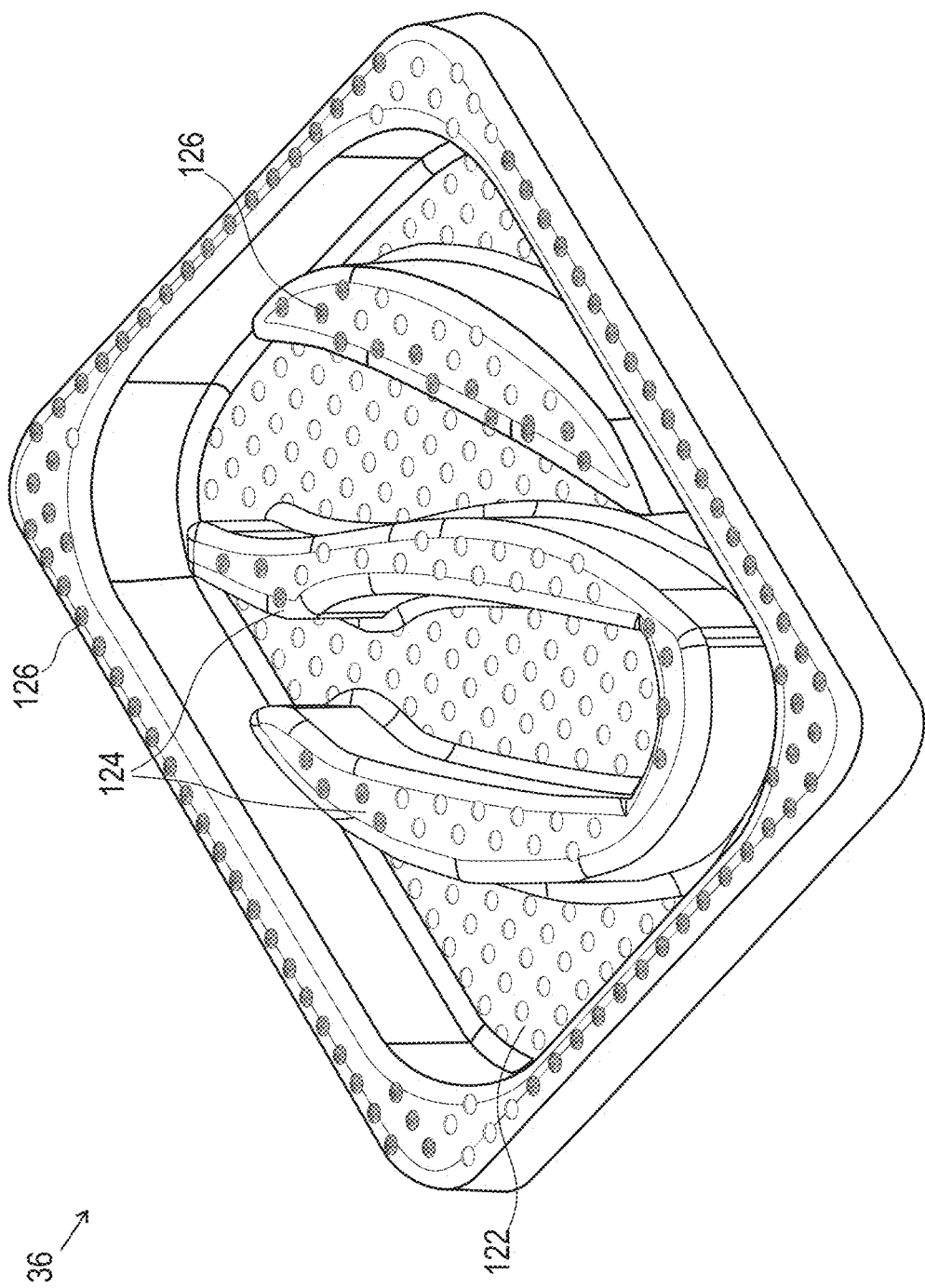
FIG. 19 illustrates a perspective view of an embodiment of the tray of FIG. 17. In this embodiment, the tray is shown having a plurality of apertures to facilitate drainage of fluids.
Figure 20:
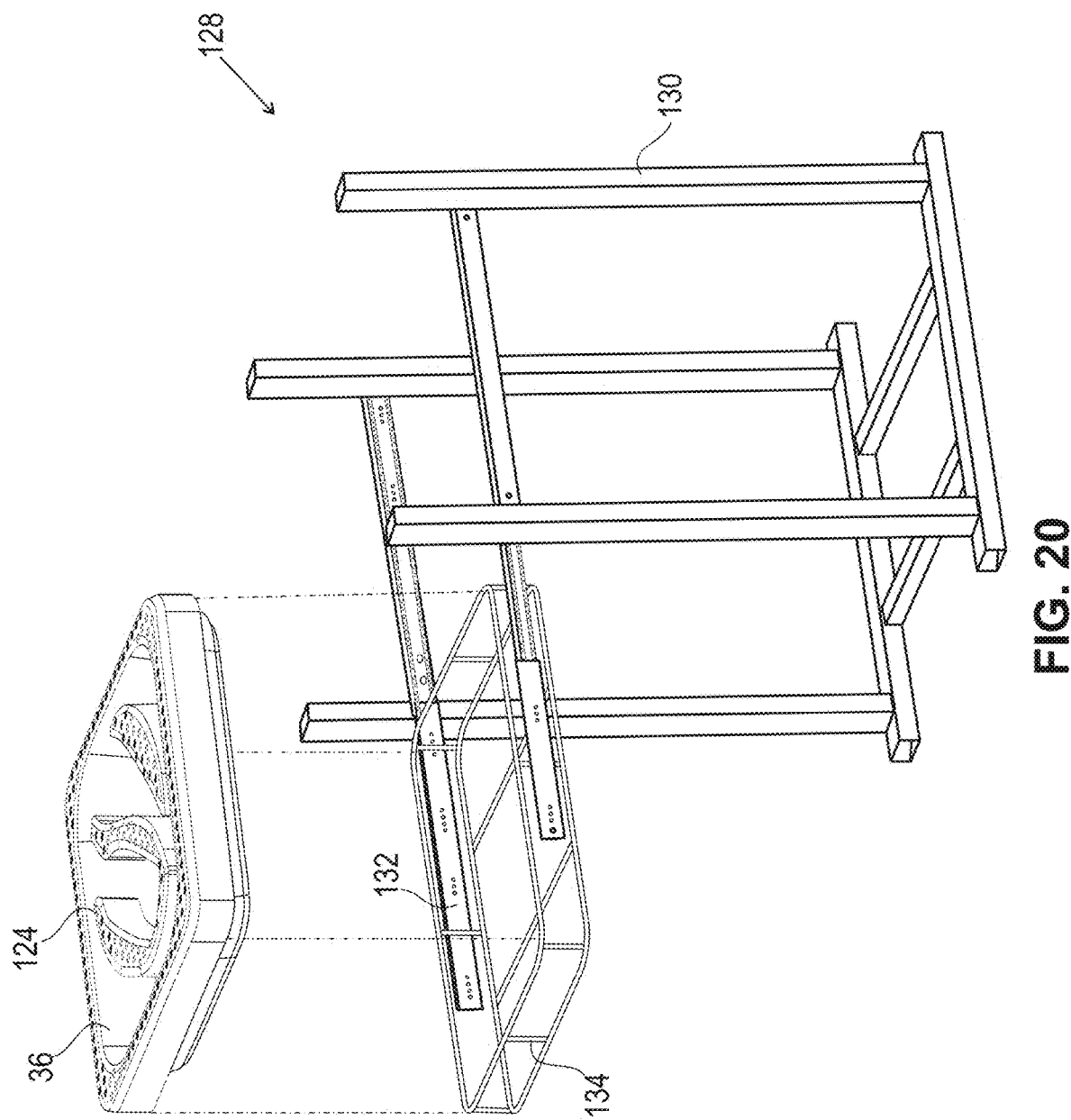
FIG. 20 illustrates a perspective view of the tray of FIG. 19 configured to be disposed within a cart having a runner assembly configured to receive the tray.

In some embodiments, the tray can have a plurality of apertures, such as holes 126 to facilitate drainage of fluids, as shown in FIGS. 19 and 20. In some embodiments, when the tray includes a plurality of apertures, the tray is configured to be stored in a cart 128, as shown in FIG. 20. The cart comprises a housing 130 having a runner assembly 132 configured to receive the tray. The timer will be coupled to the housing, slot, lid and/or the tray, as described above. In some embodiments, the tray corresponds to a particular runner assembly of the cart and the runner assembly corresponds to a particular tray 36.

For example, the cart can have a frame 134 configured to receive the tray. In practice, in some embodiments, the user places the tray in the frame and the tray will be nested within the frame and the frame will partially enclose at least a portion of the exterior surface of the tray. The frame, in some embodiments, can correspond to a specific tray so that another tray would not be able to be nested within the frame. In this way, the tray can be specific for that specific frame and, therefore, fit in the specific slot to maintain the desired environment for the endoscope and/or tray. In other embodiments, the frame can be universally adaptable to any tray type.

In some embodiments, the tray is disposable and is configured to be engaged by a disposable liner 136 and a disposable cover 138, as shown in FIG. 16. In some embodiments, the disposable liner and disposable cover are similar to the liner and cover found and described in U.S. U.S. Pat. No. 6,749,063, assigned to Cantel (UK) Limited. This patent is incorporated herein by reference.

In some embodiments, the tray interior and portions of the exterior of the tray can be engaged by a liner. The liner can be made of a flexibly deformable material substantially impermeable to fluids.

In some embodiments, the disposable liner contacts the bottom surface of the tray and at least partially encloses the reprocessed endoscope. In some embodiments, the liner is a disposable single use liner that may be sterile or unsterile.

In some embodiments, the disposable liner is configured to temporarily line the entirety of the interior compartment of the tray and prevents the endoscope from having direct contact with the interior of the tray. In some embodiments, the liner prevents moisture from the reprocessed endoscope from contacting the tray and when the tray is used repeatedly, it prevents or reduces contamination from one endoscope to the next endoscope.

The tray whether it is lined or not lined can be temporarily covered with a disposable cover. In some embodiments, the disposable cover at least partially encloses the reprocessed endoscope and the tray. In some embodiments, the cover is a disposable single use cover that may be sterile or unsterile.

The cover for the endoscope storage tray can comprise a flexibly deformable sheet material substantially impermeable to fluids, the flexibly deformable sheet material configured to be temporarily secured to the endoscope storage tray so as to cover at least an interior of the endoscope storage tray.

In some embodiments, the cover can be a reversible pouch, as shown in FIG. 18. The reversible pouch is configured to entirely enclose the tray. In some embodiments, the reversible pouch can have a clean/green colored side 140 and a biohazard/red side 142. In some embodiments, the clean/green side can have indicia 144 in the form of a word, words and/or a symbol. For example, the indicia can be the word "CLEAN". In some embodiments, the biohazard/red side can have indicia 144 in the form of a word, words and/or a symbol. For example, the indicia can be the word "BIOHAZARD". When the tray is inserted into the cart and the clean/green side is facing upward, this can indicate to a user that the endoscope is clean and ready for use. When the tray is inserted into the cart and the biohazard/red side is facing upward, this can indicate to a user that the endoscope is contaminated, should not be used and that the endoscope needs to be reprocessed. In some embodiments, the reversible pouch can have a clear/transparent viewing window 146 in the center of each side of the pouch. In some embodiments, the reversible pouch can be sealed by a zipper.

In some embodiments, the cover is configured to maintain the quality of the HLDS by limiting the endoscope's exposure to contaminants from the outside environment of the tray. In this way, the cover will decrease the amount of contaminants that can settle on the exterior of the endoscope or in the internal channels of the endoscope that originated from the outside environment. In some embodiments, the tray is configured to engage the rim, walls and/or bottom surface of the cover.

In some embodiments, the cover can be manufactured in different colors such as in a green or a clear color to indicate that the endoscope is clean and ready for use. Alternative colors can be selected such as blue, pink, yellow, red, orange, brown or black. In some embodiments, the cover can be reversible and a different color can be used on the inner surface than on the outer surface of the cover.

In some embodiments, the tray, the disposable liner and the disposable cover are substantially impermeable to fluids, such as, for example, bodily fluids. In some embodiments, the disposable liner and the disposable cover are made from one or more biodegradable materials.

In some embodiments, the cover can have a rectangular shape to correspond with the shape of the tray but other cover shapes are contemplated depending on tray shape. These shapes include oval, square, circular or the like.

In some embodiments, a sensor 148 is provided that is configured to be disposed in the slot, as shown in FIG. 3 and/or other components of the housing. In some embodiments, the sensor can be coupled to the timer and the timer is activated when the tray is inserted into the slot. In some embodiments, the sensor is a weight sensor, an optical sensor and/or a pressure sensor.

The sensor can be wired or wirelessly coupled to a computer 150 that can serve to generally control operation of the cart to make it a Smart Cart. In addition to or alternatively, the sensor can be coupled to the housing, tray, and/or slot.

The computer has a data logging module that, among other things, allows input from the timer, the sensor, the tracking component of the endoscope, the locking component of the endoscope, and will provide indicia on the status of the endoscope, the lock, and if a tray is loaded in the slot.

The computer will generally comprise a circuit board including a processor and associated electronics. The processor may be of any type known to those of ordinary skill in the art and may, in some embodiments, comprise a general purpose processor running software programs in an attached memory, or may comprise a single purpose processor specifically programmed or built to control the functions of the cart described herein. The computer will also include other electronics and components necessary to operate and to take in and interpret data from the sensor, which can be one or more weight sensors, optical sensors and/or pressure sensors. The computer may also include associated memory and storage for storing data including the tray identification, endoscope identification and its parts (e.g., valves), timer, pressure, weight, optical sensors data, before and after use and operational information or for storing or interpreting calibration information.

The computer may also include systems for connecting computing devices, both via networks and using hookups for portable devices, or for connecting with hard copy generation systems such as printer or other hard copy generator. The computer may comprise any form of display known to those of ordinary skill in the art. In an embodiment, the display will comprise a screen such as, but not limited to, an LCD touch screen capable of both providing a visual indicator of information. The computer may also include indicators or lights to provide specific information in that fashion. In addition to providing information to the user, the computer may also take input from a user such as by them pushing buttons, activating timers, turning knobs, flipping switches or otherwise acting on actuators. The computer may also additionally or alternatively comprise devices capable of generating or understanding audible or other signals. These signals can be displayed on the cart as indicia.

In some embodiments, the sensor is configured to provide input to a microcontroller 152, shown in FIG. 1 and described herein. The microcontroller can be part of the computer. The sensor is configured to determine and transmit an indication (e.g., an electrical signal) of a measurement and/or change in measurement of weight, optics and/or pressure from the tray to detect when the tray is inserted into the slot to activate the timer. The data is then inputted or transmitted to the microcontroller from the sensor to activate the timer.

In some embodiments, when the sensor is a weight sensor, the sensor will measure the weight and/or a change in weight from when the slot is empty to when the tray is inserted into the slot and/or may otherwise be responsive to when the tray is inserted into the slot (e.g., a toggle switch responsive to insertion of the tray), and an indication is transmitted to the microcontroller to activate the timer (e.g., the microcontroller responds by activating the timer) or the user may activate the timer directly or using the computer. In some embodiments, the weight sensor will measure the weight and/or a change in weight from when the tray is empty to when the tray is full, such as when the tray is storing an endoscope, and an indication is transmitted to the microcontroller to activate the timer. The cart and/or computer may have indicia to indicate that the tray is empty or not inserted into the slot.

In some embodiments, when the sensor is an optical sensor, the sensor will measure the light and/or change in light from when the slot is empty to when the tray is inserted into the slot and/or may otherwise be responsive to when the tray is inserted into the slot, and an indication is transmitted to the microcontroller to activate the timer or the user may activate the timer directly or using the computer. The cart and/or computer may have indicia to indicate that the tray is empty or not inserted into the slot.

In some embodiments, when the sensor is a pressure sensor, the sensor will measure the pressure and/or change in pressure from when the slot is empty to when the tray is inserted into the slot and/or may otherwise be responsive to when the tray is inserted into the slot, and an indication is transmitted to the microcontroller to activate the timer. In some embodiments, the pressure sensor will measure the pressure and/or change in pressure from when the tray is empty to when the tray is full and/or may otherwise be responsive to when the tray is full, such as when the tray is storing an endoscope, and an indication is transmitted to the microcontroller to activate the timer or the user may activate the timer directly or using the computer. The cart and/or computer may have indicia to indicate that the tray is empty or not inserted into the slot.

In some embodiments, the slot and/or components of the housing can have more than one sensor. In some embodiments, each slot and/or other components of the housing can have 1, 2, 3, 4, 5, 6, 7, 8, 9, to 10 sensors.

In some embodiments, the microcontroller and/or the sensor can be powered by an electrical source that provides direct current (DC) in the form of a battery, and cycles between an active mode and a sleep mode in order to conserve battery life of the microcontroller and/or the sensor. In some embodiments, the microcontroller and/or the sensor can be powered by an electrical source that provides alternating current (AC) in the form of a wall outlet.

In some embodiments, the cart comprises a display 154 that indicates whether a tray is slidably received in the slot, as shown in FIGS. 1 and 4. The display can be a digital display.

Figure 21:
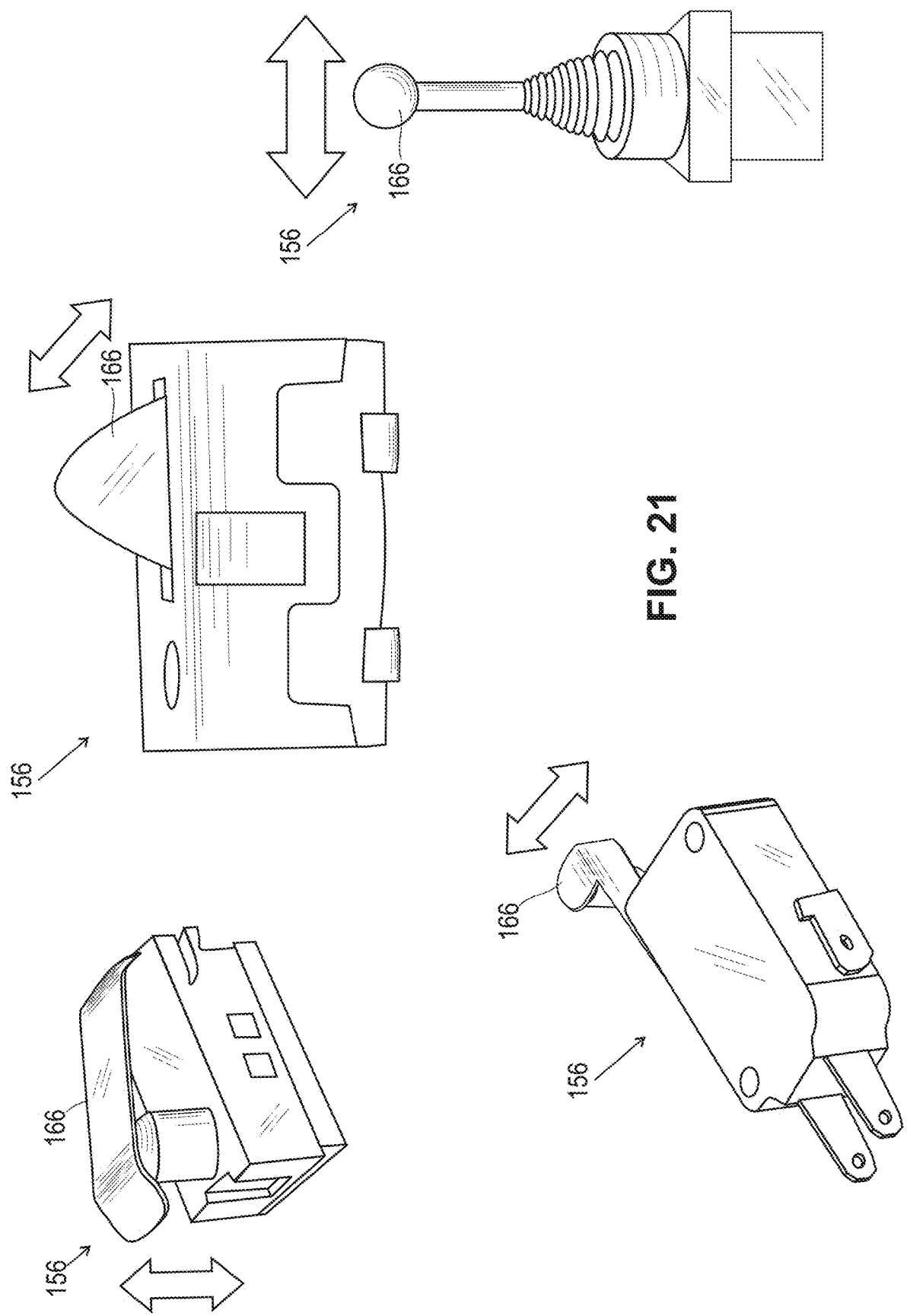
FIG. 21 illustrates a perspective view of multiple timer switches that can be used in the cart for switching on the timer of the cart once the tray is loaded in the cart and moves the switch to start the timer.
Figure 22:
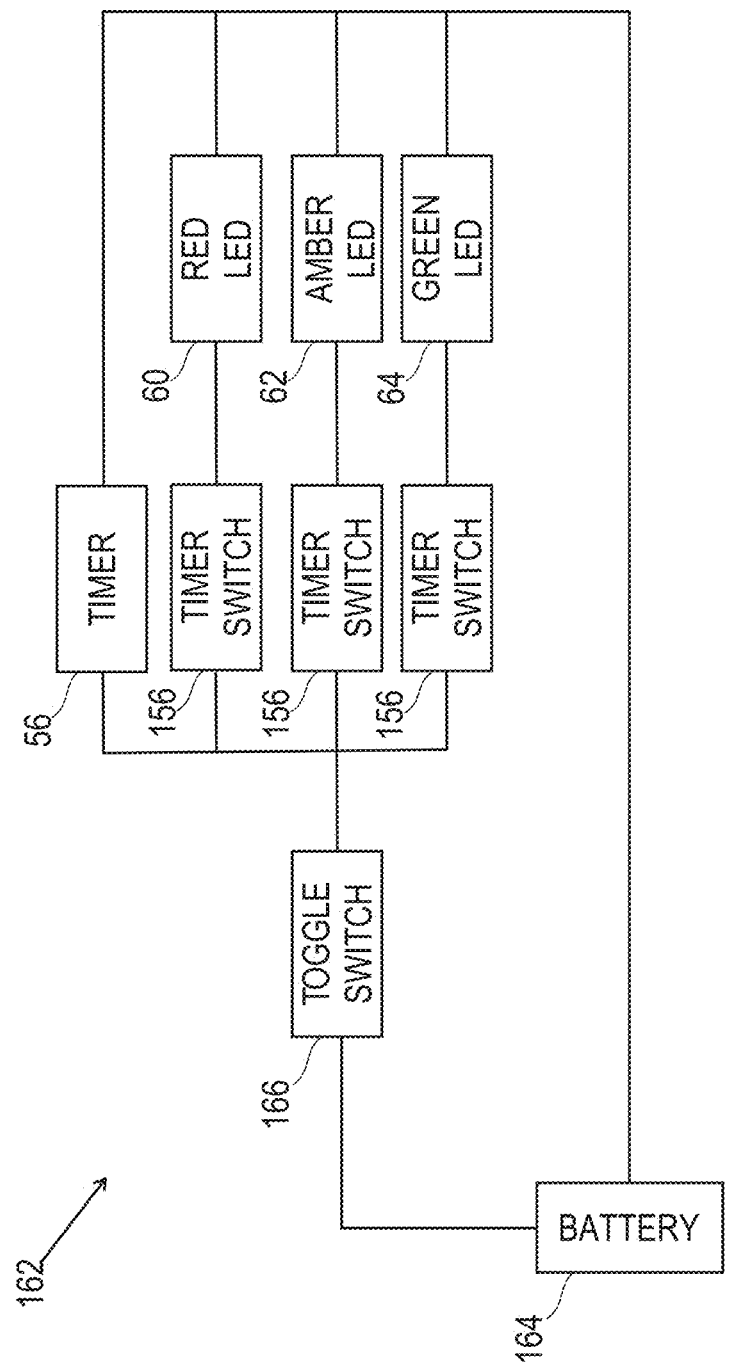
FIG. 22 illustrates a schematic of a timer switch for the timer of the cart of FIG. 1 and its output on the display of, for example, red, amber and green.
Figure 23:
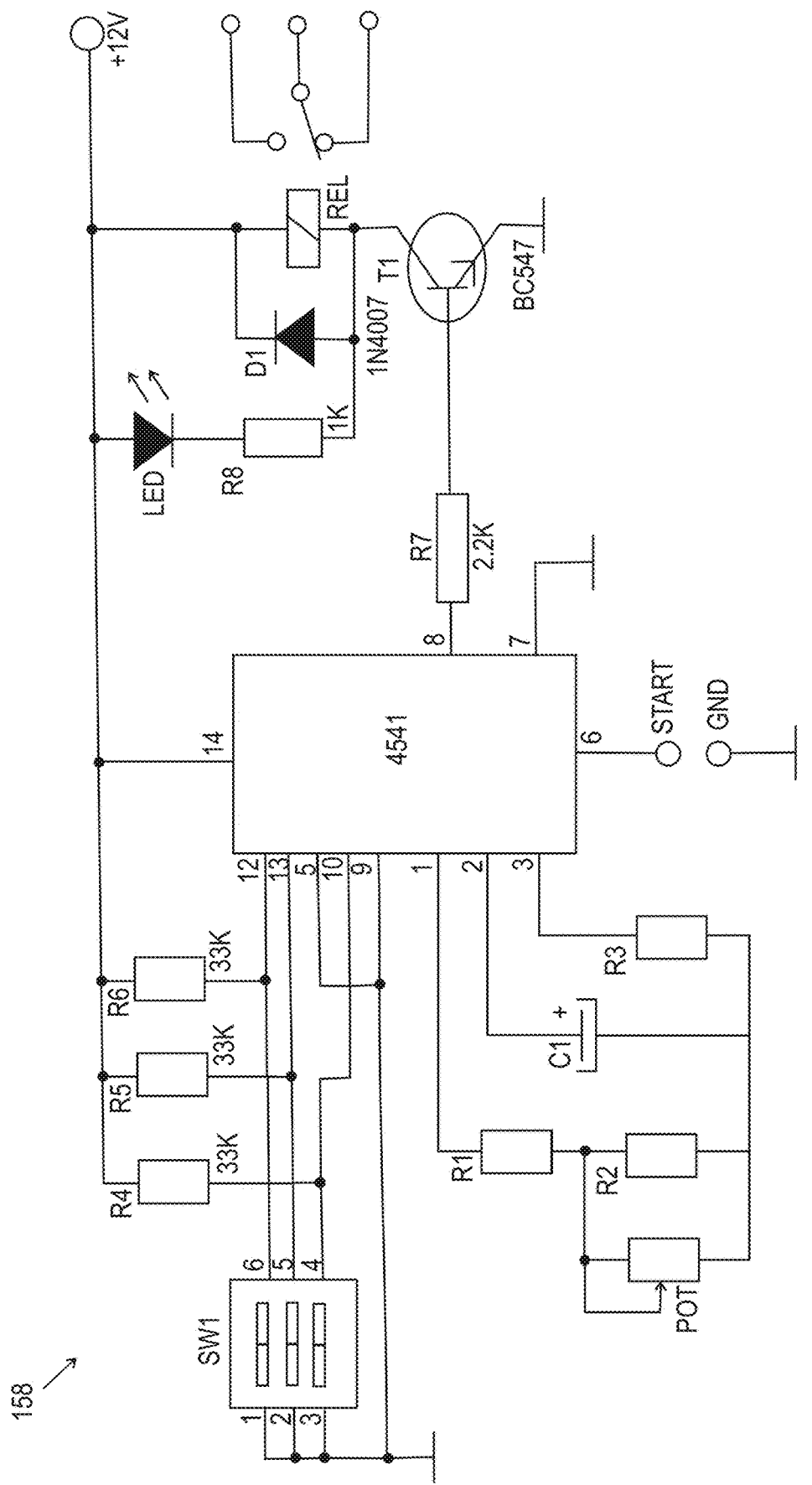
FIG. 23 illustrates a schematic of a timer relay circuit for the timer of the cart of FIG. 1.
Figure 24:
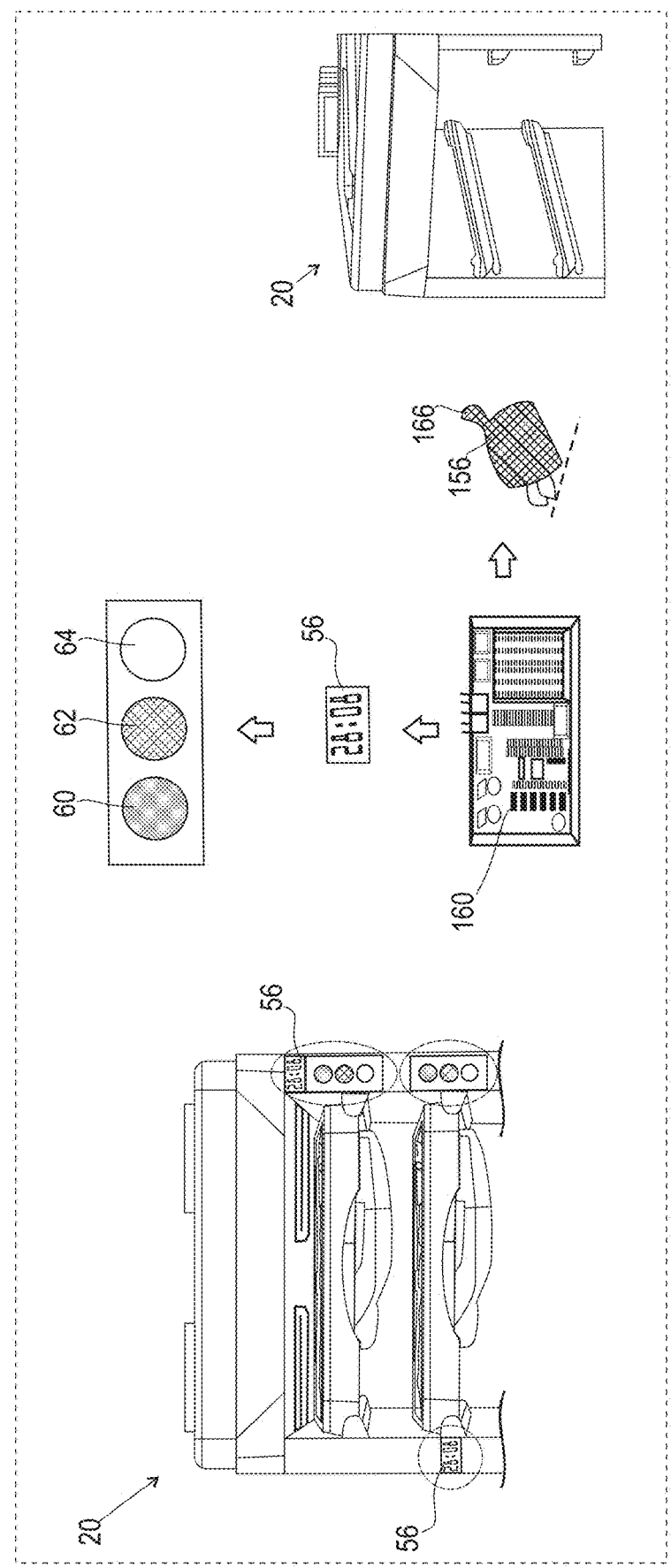
FIG. 24 illustrates a perspective view of the cart of FIG. 1 comprising the timer switches of FIG. 21 that work in conjunction with the timer and have the output showing indicia for time increments.

In some embodiments, timer switches 156, as shown in FIG. 21, can operate as the sensor (e.g., toggle switch/pressure sensor responsive to tray insertion into the cart), work in conjunction with the sensor or be independent from the sensor. In some embodiments, the timer switches and/or the sensor are wired to a relay circuit 158 on a circuit board 160, as shown in FIGS. 23 and 24 to activate the timer and to initiate the timer to display the indicia 58, such as light indicia, as shown in schematic 162 of FIG. 22. In the schematic, a battery 164 is depicted that supplies power to a toggle switch 166 paired to one or more timer switches 156. Once the toggle switch is activated, the timer 56 activates the timer switches 156 to produce the indicia 58 at different periods of time, and the indicia can be in the form of red light 60, amber light 62 and green light 64.

FIG. 23 illustrates a schematic of a timer relay circuit in accordance with some embodiments. As shown, switches SW1 may be utilized for setting an operation of a timer, such as a CD4541B programmable timer available from Texas Instruments. In operation, the timer may be activated to maintain a light emitting diode (LED), for example to produce the green light until the end of a period of time, such as three hours, to indicate that the endoscope is available for use during the period of time. At the end of the period of time, the LED may be turned off and a further LED may be lit through use of an additional timer circuit, for example producing the red light, indicating that the endoscope is no longer available for use. The amber light may be similarly produced as desired during a further period of time.

Figure 25:
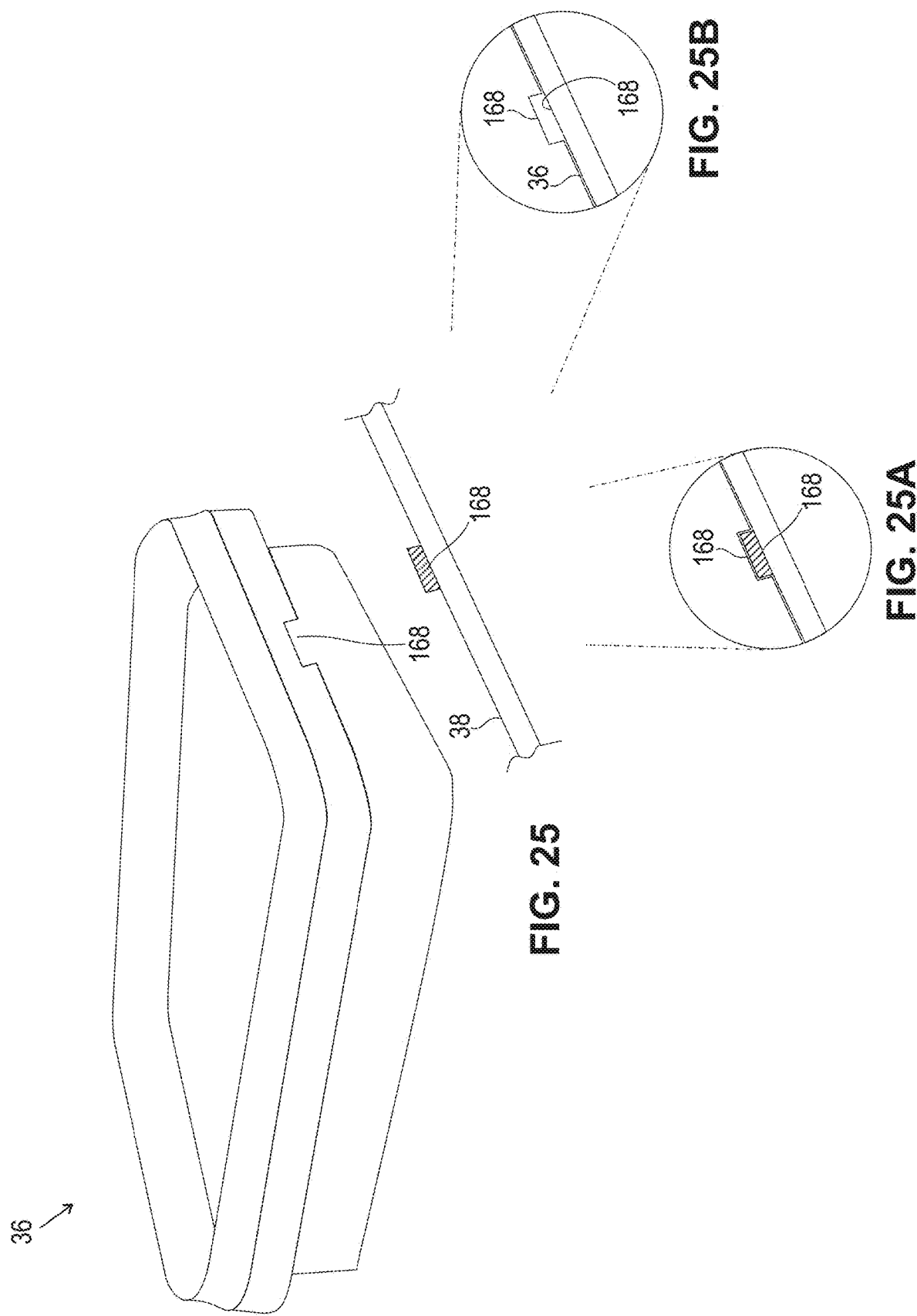
FIG. 25 illustrates a perspective view of a locking surface on the tray and a locking surface on the slot that are configured to matingly engage to lock the tray into the cart.

In some embodiments, the slot, the tray and/or the housing comprises a locking surface 168 to lock the tray into the cart, as shown in FIGS. 3 and 25-25B. In some embodiments, the locking surface of the tray, such as a recess mates with a locking surface 168 of the slot such as a projection, as shown in FIG. 25A to lock the tray into the cart. In some embodiments, the locking surface of the slot disengages with the locking surface of the tray, as shown in FIG. 25B to unlock the tray from the cart. In some embodiments, the tray can be locked into the slot when the endoscope needs to be reprocessed. In some embodiments, the tray with an endoscope that needs to be reprocessed can be unlocked from the slot, have a red cover added to the tray, and then have the tray be replaced by a tray that contains a new reprocessed endoscope having a green cover.

In some embodiments, the slot, the tray and/or the housing includes a locking surface that includes a solenoid, a cam lock, a pin lock, an electro-magnetic lock, a mechanical clamp, a ratchet lock or a latch to lock the locking surface of the tray and/or the slot. In some embodiments, the locking surface can be a manual lock that can be locked with a key by the user after a period of time has expired, indicating that the endoscope needs to be reprocessed.

In some embodiments, when the timer displays a red light to indicate that the endoscope needs to be reprocessed after a time increment, the tray is locked in the slot by the mating engagement of the locking surfaces. In some embodiments, the timer displays the amber light before the tray is locked in the slot, the timer displays the red light when the tray is locked in the slot, and the timer displays the green light when the tray is unlocked in the slot.

Figure 26:
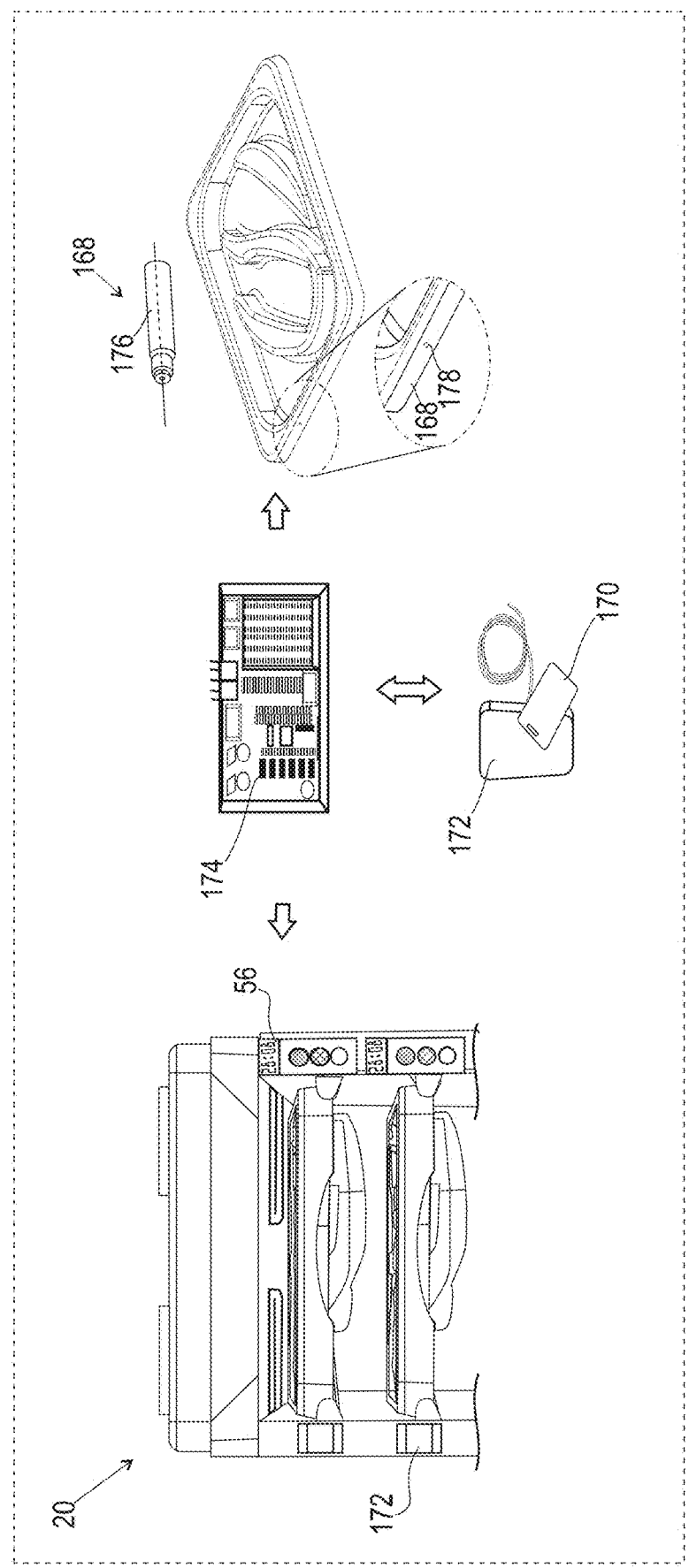
FIG. 26 illustrates a perspective view of a portion of the cart of FIG. 1 that utilizes a pass key/proximity key and a proximity reader to lock and unlock the tray or trays into the cart.
Figure 27:
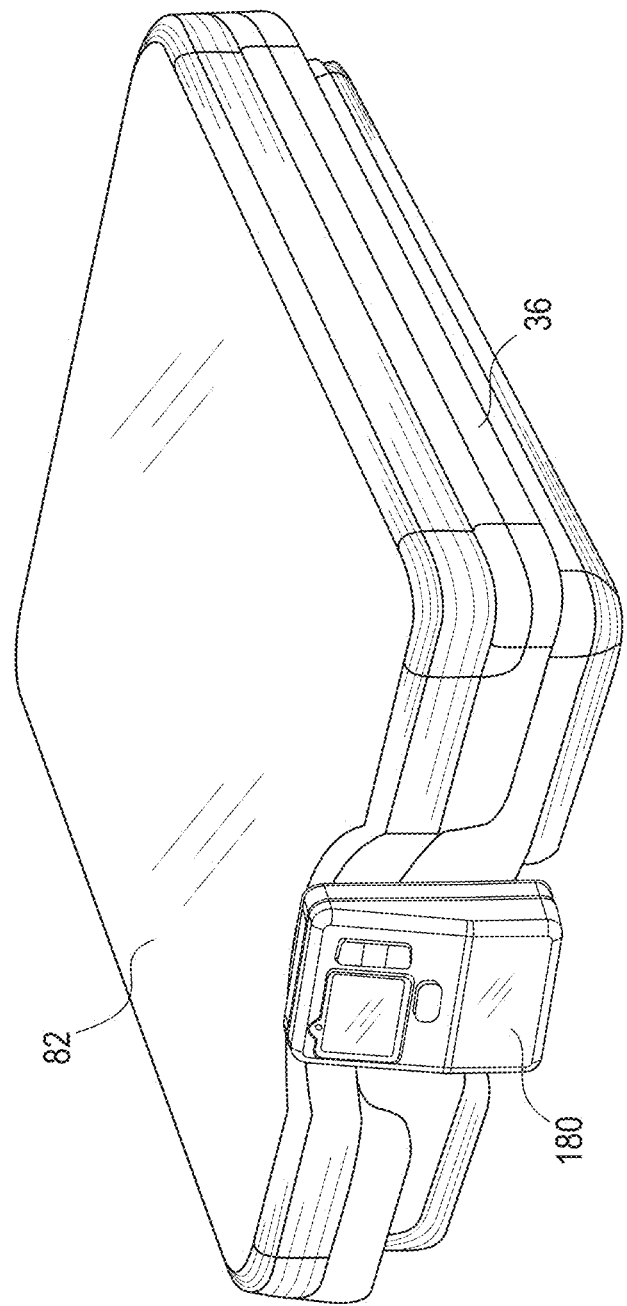
FIG. 27 illustrates a perspective view of an embodiment of the tray and an embodiment of the rigid lid having locking surfaces that engage with locking surfaces of a removable timer lock.
Figure 28B:
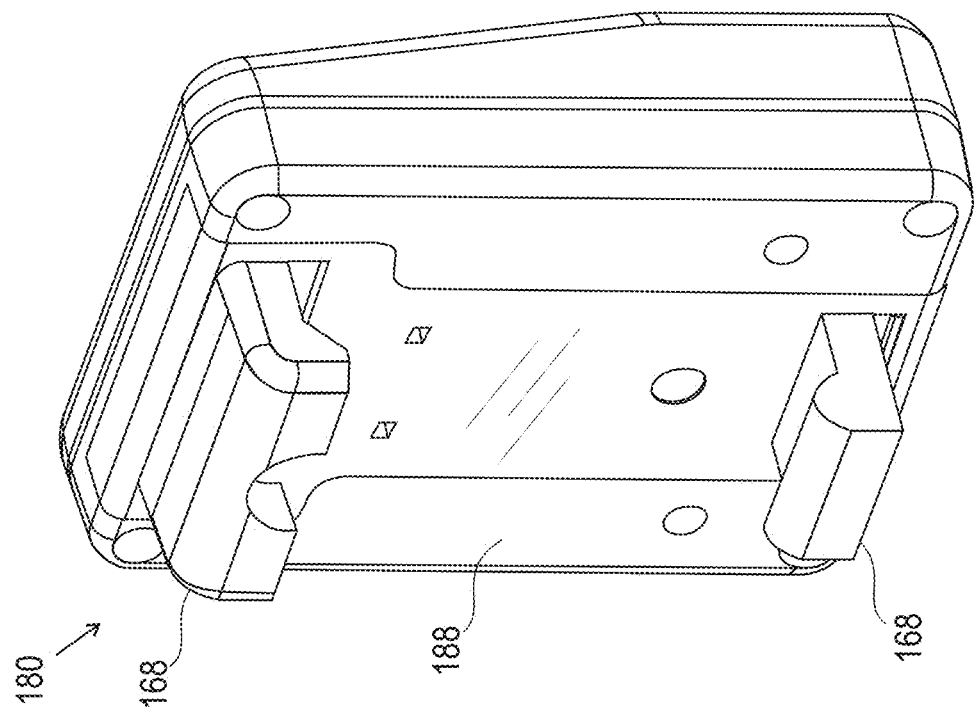
FIG. 28B illustrates a perspective back view of the removable timer lock of FIG. 27.
Figure 28A:
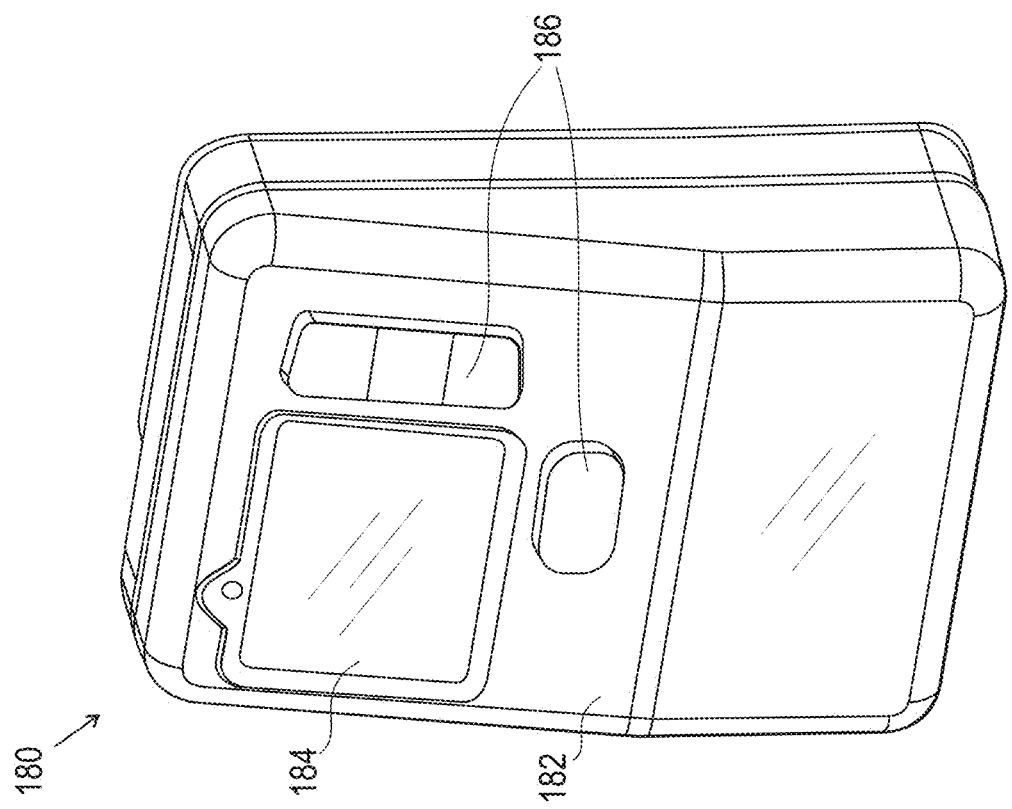
FIG. 28A illustrates a perspective front view of the removable timer lock of FIG. 27.

In some embodiments, as shown in FIG. 26, a pass key 170 can be used to deactivate the locking surface of the slot and/or the tray and unlocks the tray for removal from the cart. The pass key can also be used to activate the locking surface of the slot and/or tray and lock the tray into the slot. The pass key can be a proximity card that works in conjunction with a proximity reader 172. The pass key or proximity card is embedded with either a barcode, magnetic strip, computer chip or another storage medium that is read by the proximity reader.

The proximity reader includes a circuit board 174 that reads the pass key or proximity card and also controls whether the trays will be locked or unlocked. In some embodiments, the proximity reader uses a wireless radio frequency such as Bluetooth® technology or Near Field Communication (NFC) technology to read the passkey or proximity reader. The proximity reader emits pulses of the wireless radio frequency that the built-in passive chip uses to power the pass key or proximity card.

In some embodiments, when the pass key or proximity card combined with the proximity reader is used, the locking surface includes a solenoid 176 paired to a locking surface on the tray that is indented 178.

In some embodiments, as shown in FIGS. 27-33, the rigid lid and the tray can be locked together with a timer lock 180 that is removable. The timer lock is configured to lock and unlock the lid from the tray when a predetermined amount of time has passed or expired which has been programmed into the timer lock. In some embodiments, the timer lock cannot be unlocked and/or locked unless a specific code is entered. As shown in FIG. 28A, the timer lock includes a front face 182 that includes a display 184 that visually indicates the amount of time that the endoscope is stored in the tray. Buttons 186 are located adjacent to the display which are used to set the timer lock for use. As shown in FIG. 28B, a back surface 188 of the timer lock includes locking surfaces 168 in the form of 2 opposing movable flanges. The locking surfaces of the timer lock are configured to engage with locking surfaces 168 on the tray and the lid, in the form of indents, as shown in FIGS. 29-33. In some embodiments, alternatively, the locking surfaces of the timer lock are recesses and the locking surfaces of the tray and/or the lid are movable flanges.

Figure 33:
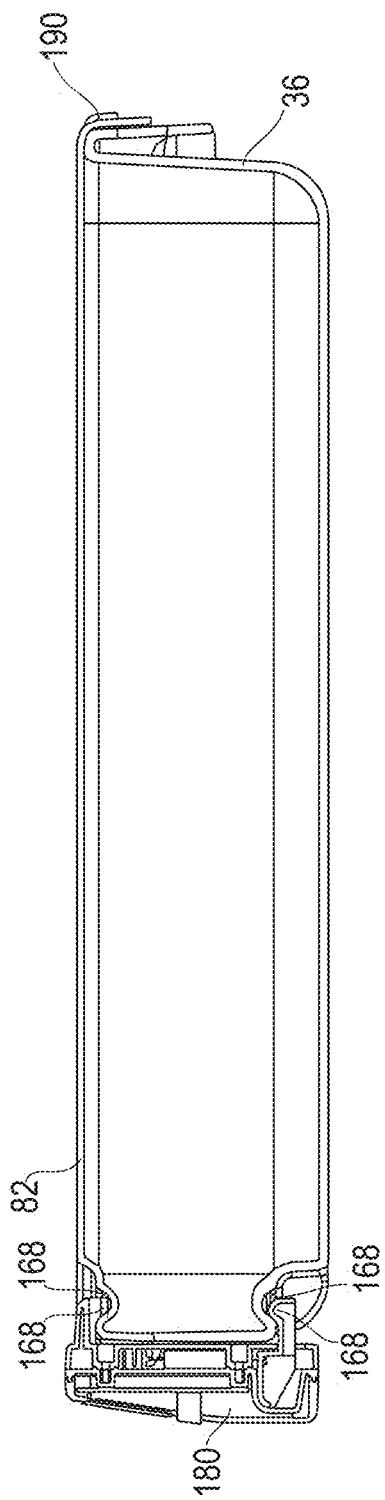
FIG. 33 illustrates a cross sectional side view of the timer lock engaged with the tray and rigid lid of FIG. 27.

The rigid lid can removably engage with the tray, as shown in FIGS. 27, 30, 32 and 33. As shown in FIGS. 30 and 33, the tray can include projections 190, for example 2 projections that are located on the rim of the tray that correspond with recesses 192, for example 2 recesses that are located on the rim of the rigid lid. A user can engage the rigid lid with the tray by inserting the projections of the tray into the recesses of the rigid lid. Once the rigid lid is engaged with the tray, the timer lock can be attached to the rigid lid and the tray at the locking surfaces, as shown in FIG. 33. It is to be understood that the timer lock can alternatively be a lock only or a timer only. Further, the timer lock combined with the tray and lid can be inserted into the cart or can be a stand-alone configuration without the need for a cart.

Figure 34:
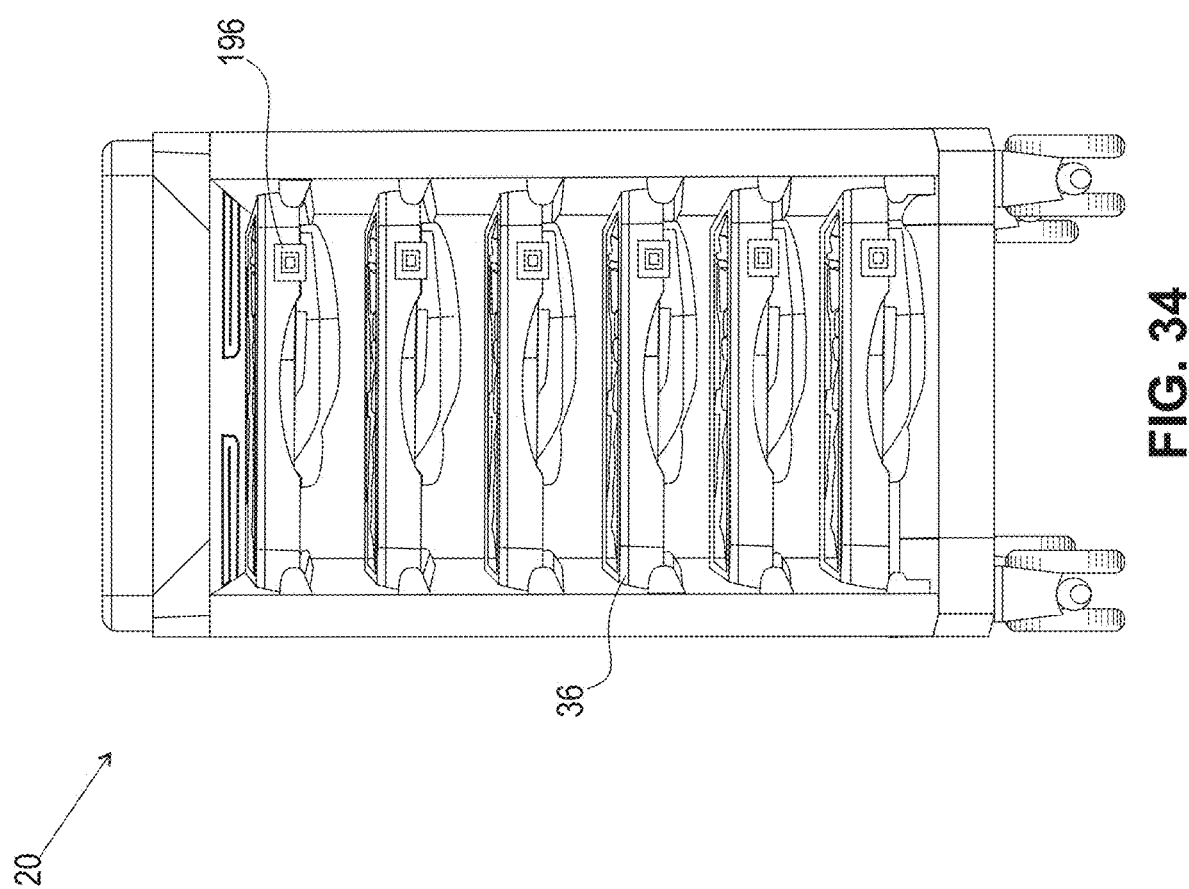
FIG. 34 illustrates a front view of an embodiment of the cart of FIG. 1 where the cart includes a radio-frequency identification (RFID) reader and the tray includes a RFID tag so that the tray can be tracked.
Figure 35:
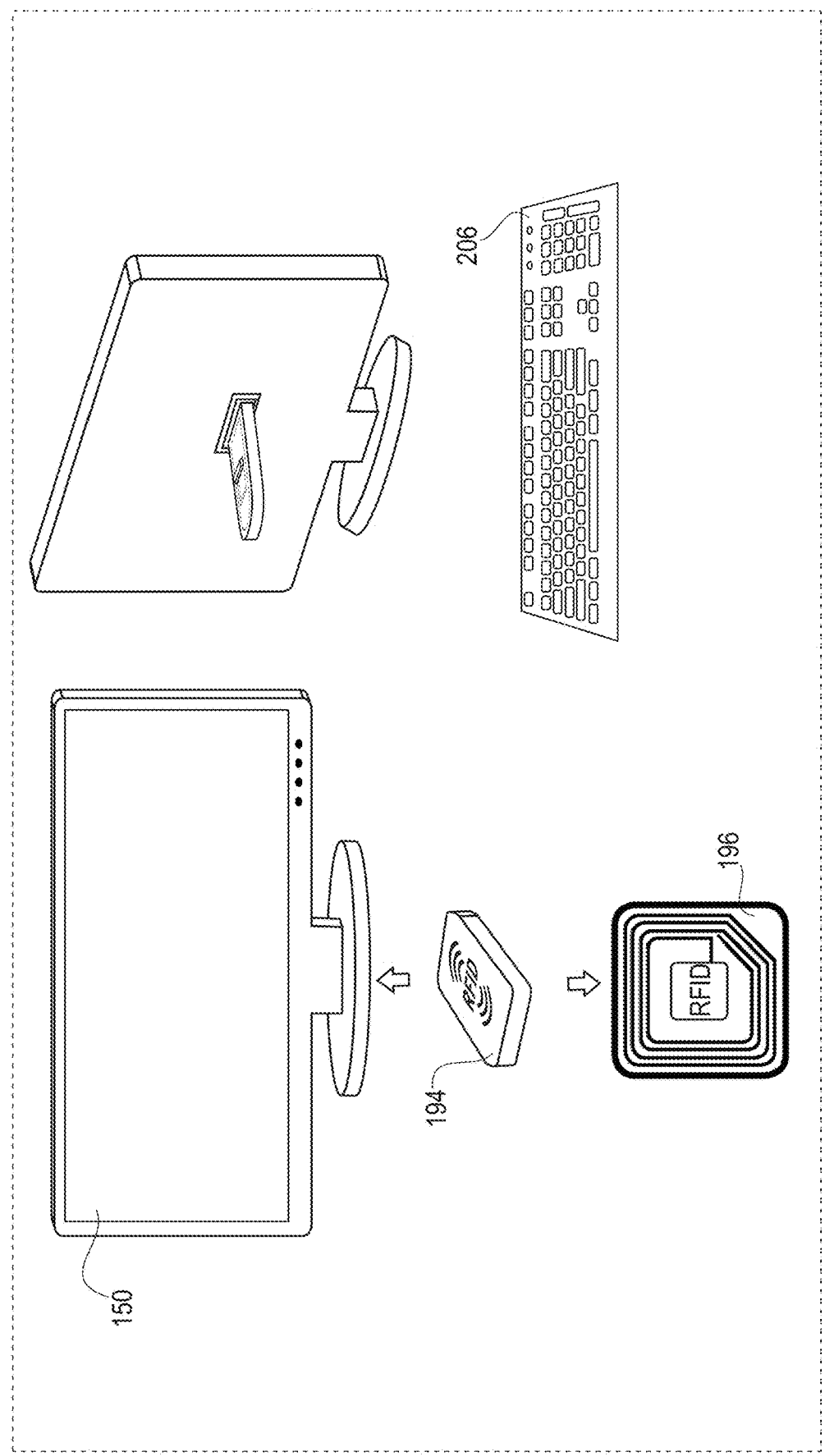
FIG. 35 illustrates a perspective view of the RFID reader and the RFID tag transmitting data obtained from the RFID reader to a personal computer.

In some embodiments, as shown in FIGS. 34 and 35, the cart can include a radio-frequency identification (RFID) reader 194 and the tray includes a RFID tag 196 so that the tray can be tracked. The RFID reader can be connected to a personal computer (PC) 150 such as, for example, network/stand-alone computers, personal digital assistants (PDAs), WebTV (or other Internet-only) terminals, set-top boxes, cellular/phones, screen phones, pagers, blackberry, smart phones, iPhone, iPad, table, peer/non-peer technologies, kiosks, or other known (wired or wireless) communication devices, etc. The RFID reader can also be a separate handheld device.

In some embodiments, the location of the tray and/or the exact endoscope located in the tray can be tracked by the RFID reader since the RFID tag will store this information. In some embodiments, the time and date that the endoscope was reprocessed can be stored on the RFID tag. In some embodiments, the PC can have a specific software application that is tailored to read and share the data collected.

In some embodiments, the RFID tag can be a read-write, read-only or "write once, read many" (WORM). In some embodiments, with read-write chips, information or data relating to a specific endoscope, tray and/or cart can be added to the RFID tag or write over existing information when the tag is within range of the RFID reader. Read-write tags can have a serial number that can't be written over. Additional blocks of data can be used to store additional information about the specific endoscope, tray and/or cart that the tag is attached to (these can usually be locked to prevent overwriting of data). In some embodiments, read-only microchips have information stored on them during the manufacturing process. The information on such chips can never be changed. WORM tags can have a serial number written to them once, and that information cannot be overwritten later.

Figure 37:
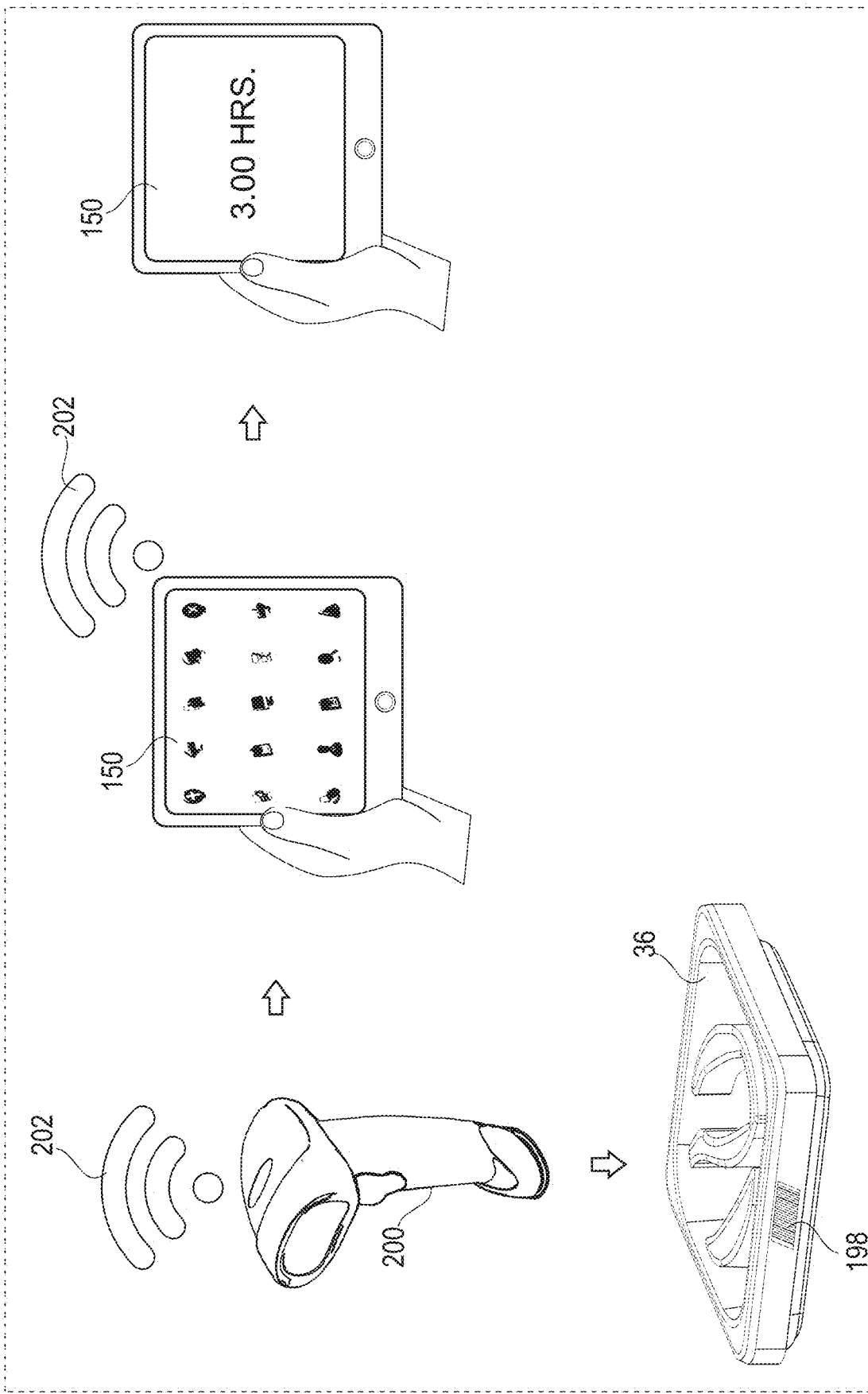
FIG. 37 illustrates a perspective view of the barcode and barcode reader of FIG. 36. The data obtained from the barcode reader is shown transmitted to a personal computer, such as a smartphone, tablet or portable computer.

In some embodiments, as shown in FIGS. 36 and 37, the tray can include a barcode 198 and the cart can include a wireless barcode reader 200 so that the tray can be tracked. In some embodiments, the wireless barcode reader can transmit data read from the barcode to a PC. The data can be transmitted through wireless radio frequency 202 such as Bluetooth® technology, as shown in FIG. 37. In some embodiments, the location of the tray and/or the exact endoscope located in the tray, the time and/or the date that the endoscope was reprocessed can be stored and tracked by the barcode and wireless barcode reader.

Figure 38:
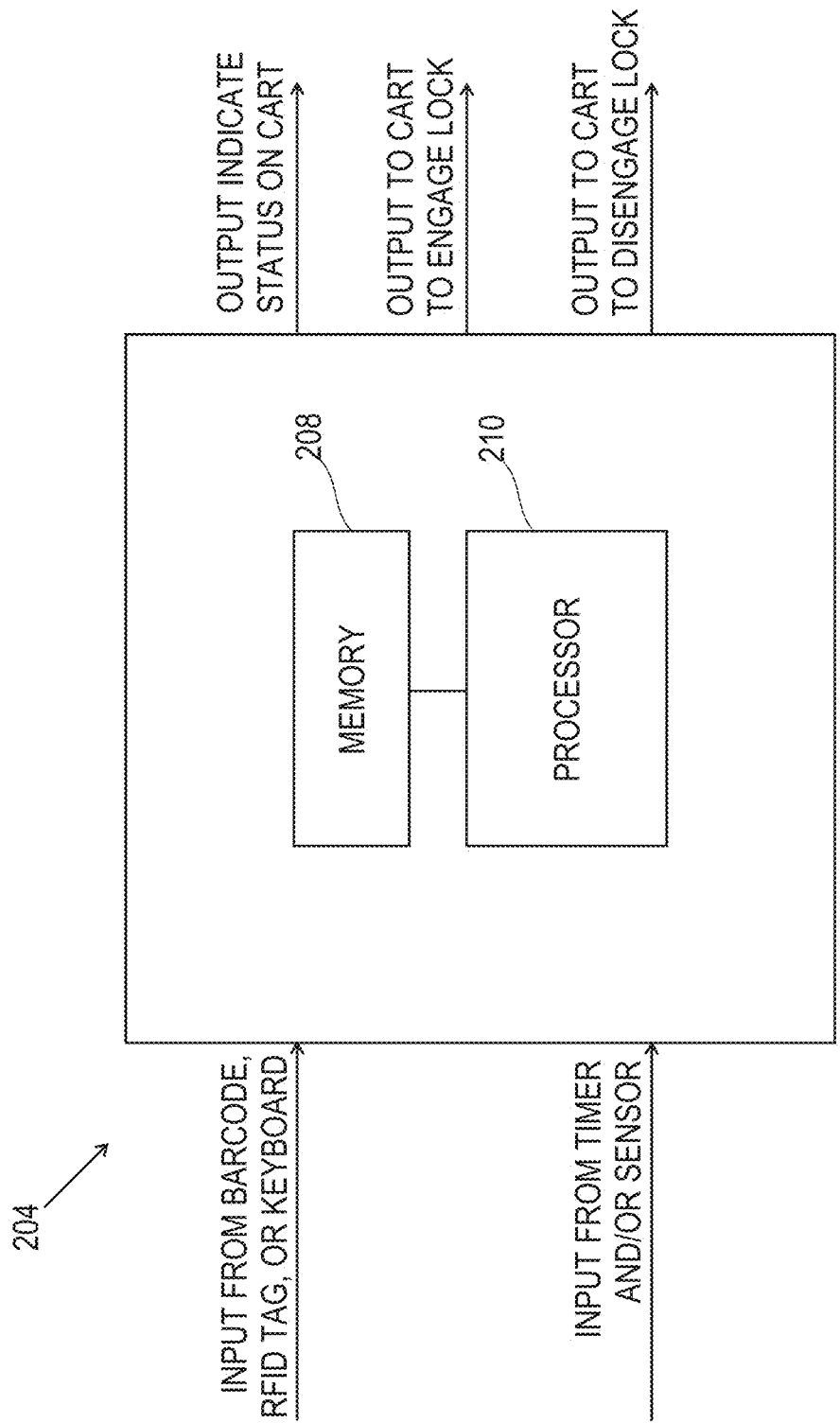
FIG. 38 illustrates a block diagram of a data logging module in the cart of FIG. 1 that can identify, track and inventory endoscopes in the cart.

In some embodiments, the cart is linked wirelessly or is directly wired to a computer system that comprises a data logging module 204, as shown in FIG. 38 to identify, track and inventory endoscopes, as well as obtain data from the sensor and timer of the cart. A memory 208 may include instructions for programming a processor 210, controller, etc., for operation in accordance with some embodiments and/or may also store a status of one or more endoscopes, trays, etc. The processor may in operation receive input including one or more from a barcode scanner, RFID tag, keyboard, etc., as well as input from a timer and/or sensor for producing status indicia for the cart/tray(s) as well as for controlling a locking/unlocking of trays.

The computer, among other things, allows input from the timer, the sensor, the tracking component of the endoscope, and/or the locking component of the endoscope, and will provide indicia on the status of the endoscope, the lock, and/or if a tray is loaded in the slot. The computer will generally comprise a circuit board including a processor and associated electronics. The processor may be of any type known to those of ordinary skill in the art and may, in an embodiment, comprise a general purpose processor running software programs in an attached memory, or may comprise a single purpose processor specifically programmed or built to control the functions of the cart described herein. The computer will also include other electronics and components necessary to operate and to take in and interpret data from the sensor, which can be one or more weight sensors, optical sensors and/or pressure sensor pressure sensors. The computer may also include associated memory and storage for storing data including the tray identification, endoscope identification and its parts (e.g., valves), timer, pressure, weight, optical sensors data, before and after use and operational information or for storing or interpreting calibration information. The computer may also include systems for connecting computing devices, both via networks and using hookups for portable devices, or for connecting with hard copy generation systems such as printer or other hard copy generator. The computer may comprise any form of display known to those of ordinary skill in the art. In an embodiment, the display will comprise a screen such as, but not limited to, an LCD touch screen capable of both providing a visual indicator of information. The computer may also include indicators or lights to provide specific information in that fashion. In addition to providing information to the user, the computer may also take input from a user such as by them pushing buttons, turning knobs, flipping switches or otherwise acting on actuators. The computer may also additionally or alternatively comprise devices capable of generating or understanding audible or other signals. These signals can be displayed on the cart as indicia.

In some embodiments, data from the data logging module can be transmitted to a cloud network or a personal computer through a wireless connection or through Wi-Fi.

In some embodiments, input from the barcode, the RFID tag, a keyboard 206 (FIG. 35) and/or input from the timer or sensor is sent to the computer having a data logging module. The data logging module comprises memory 208 and processor 210. The data logging module will output a signal to indicate the status on the cart such as to load a tray, engage the lock or to disengage the lock. This signal can be displayed on the computer display or it can be displayed as indicia on the cart, housing and/or tray. For example, output from the computer can indicate on the cart, housing and/or tray that the tray is not loaded properly in the cart or is properly loaded in the cart.

In some embodiments, output from the computer can indicate on the cart, housing and/or tray that the timer is running and the status of the reprocessed endoscope is fine (e.g., the display can show a green light). In some embodiments, output from the computer can indicate on the cart, housing and/or tray that the time for use of the endoscope is about to expire (e.g., the display can show an amber light). In some embodiments, output from the computer can indicate on the cart, housing and/or tray that the time for use of the endoscope is expired (e.g., the display can show a red light) and the cart, drawer, housing can be automatically locked and the indicator will display this as well.

In some embodiments, the data logging module can generate, record and save a message digest, which provides, among other things a user trail, electronic date and time associated with a unique identifier to identify the make, model of the endoscope and the time it was reprocessed.

In some embodiments, the cart and/or the system can comprise a computer readable storage medium which stores instructions that, when executed by the PC, cause the PC to display options for a user to enter, view, and edit some or all information/data and manage, disseminate and share information/data among users by accessing a database coupled to a user interface. In some embodiments, the database can store the information/data, and the processor will be coupled to the user interface and the database. In some embodiments, the processor will receive the information/data from the user; process and organize the information/data into the data logging module; update the database with any new information/data received from the user; and provide the updated information/data in response to an inquiry from a user.

In some embodiments, the PC can be loaded with a software program such that data collected can be stored and interfaces with the user such that data can be searched, retrieved and displayed by the user. In some embodiments, the data may be downloaded in one or more textual/graphical formats (e.g., RTF, PDF, TIFF, JPEG, STL, XML, XDFL, TXT etc.), or set for alternative delivery to the PC. The data may be displayed at a user interface, which allows viewing on the same display.

In some embodiments, the user interface can include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of the user with the data. The user interface may be directly coupled to a database or directly coupled to a network server system via the Internet or cloud computing.

In some embodiments, the user interface may be implemented as a graphical user interface (GUI) containing a display or the like, or may be a link to other user input/output devices known in the art. Individual or of a plurality of devices (e.g., network/stand-alone computers, personal digital assistants (PDAs), WebTV (or other Internet-only) terminals, set-top boxes, cellular/phones, screen phones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow the user to monitor the data. Database hardware and software can be developed for access by the user through personal computers, mainframes, and other processor-based devices. A user may access the data stored locally on hard drives, flash drives, CD-ROMs, stored on network storage devices through a local area network, or stored on remote database systems through one or more disparate network paths (e.g., the Internet).

In some embodiments, the cart, tray, lid, cover and/or liner can be made from a material such as, for example, a polymeric material. The polymeric material can be thermoplastic and/or is a polycarbonate. For example, the components described above can be fabricated from materials such as machined or injection molded thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, semi-rigid and rigid materials, elastomers, rubbers, thermoplastic elastomers, thermoset elastomers, elastomeric composites, polyphenylene, polychloroprene, polyamide, polyetherimide, polyethylene, epoxy, partially resorbable materials, totally resorbable materials, polyglycolide, polytyrosine carbonate, polycaprolactone, silicone based rubber, liquid silicone rubber, High Consistency Rubber, silicon, TPE, Polypropylene, Polycarbonate, ABS or any combination thereof. In some embodiments, the liner can be made from high-density polyethylene (HDPE) and/or low-density polyethylene (LDPE).

In some embodiments, the cart or portions of the cart can be made from one or more metals, such as for example, stainless steel alloys, commercially pure titanium, titanium alloys, Grade 5 titanium, cobalt-chrome alloys, or combinations thereof.

The components of the cart, individually or collectively, may also be fabricated from a heterogeneous material such as a combination of two or more of the above-described materials. The cart as described herein may be constructed of a suitable biocompatible material to impart various desirable characteristics, such as rigidity and resilience.

In some embodiments, components of the tray can also be made from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), plastic (e.g., polycarbonates), ABS, MABS, or the like or combinations thereof.

In some embodiments, the tray and/or the cart may be formed from a suitable material, such as polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), rubber, plastic, or the like or combinations thereof or any of the materials as described herein.

In some embodiments, contaminants can include, but are not limited to, biological contaminants such as microorganisms including bacteria, viruses, yeasts, molds and parasites; air borne contaminants such as airborne microbes; and/or chemical contaminants. In some embodiments, bacteria can include, but is not limited to *Escherichia coli*, *Klebsiella* species, *Enterobacter* species, enterococci, *Pseudomonas aeruginosa* and *Salmonella* species.

Methods

A method for storing a reprocessed endoscope is provided. The method comprises placing a tray into an endoscope storage cart, the endoscope storage cart comprising a housing having a slot configured to slidably receive the tray, the tray for storing the reprocessed endoscope; and activating a timer coupled to the housing, slot and/or tray, the timer configured to display increments of time that the reprocessed endoscope is stored in the tray. It is to be understood that the cart, tray, endoscope and timer are identical to cart 20, tray 36, endoscope 22 and timer 56 described above.

In some embodiments, the reprocessed endoscope is at least partially enclosed by a disposable liner and the tray is covered by a disposable cover. In some embodiments, the timer is manually activated by the user after the slot slidably receives the lined and covered tray.

Figure 39:
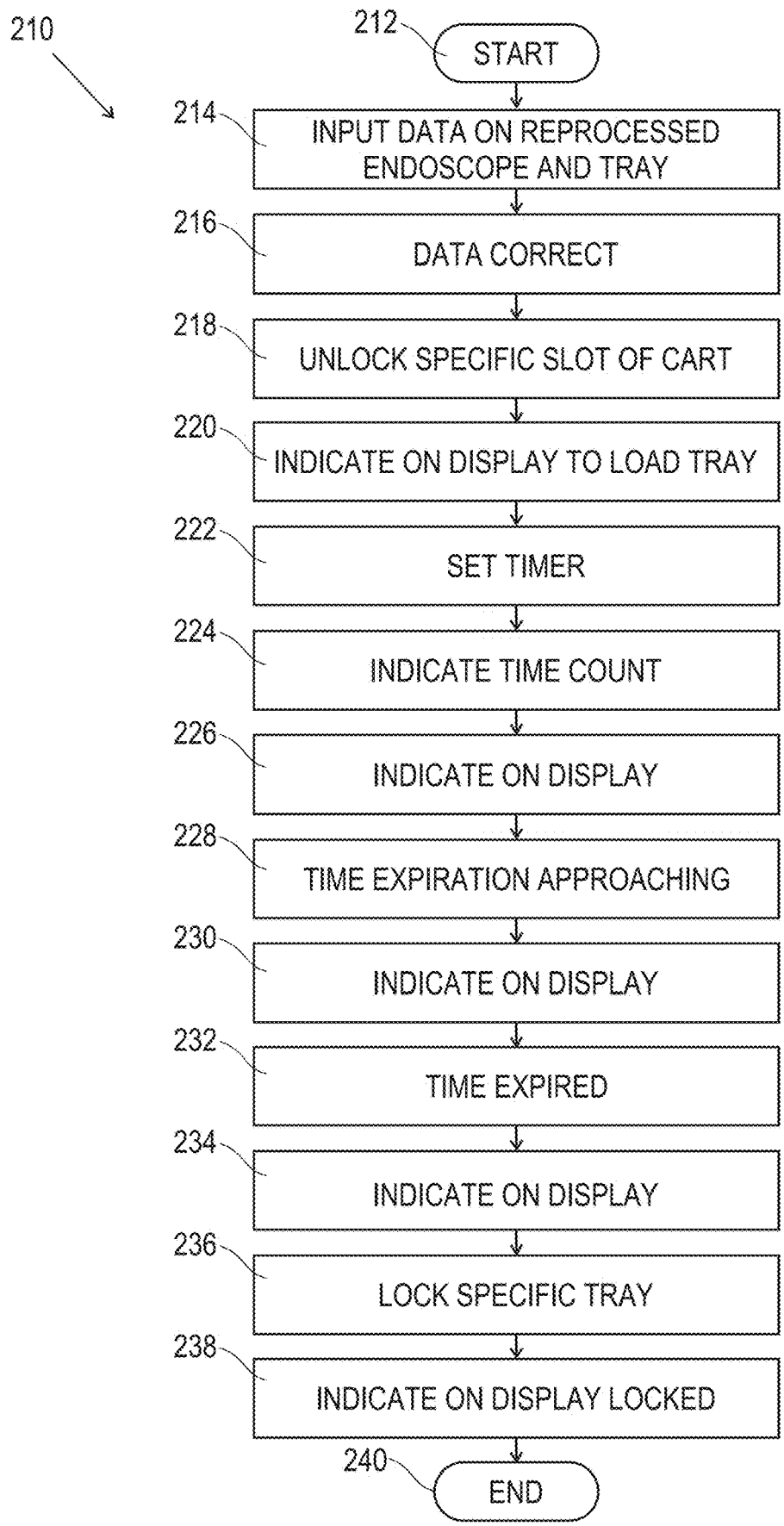
FIG. 39 illustrates a flowchart of the steps/logic that a processor undergoes to display the status of the time that the endoscope is stored and for locking and unlocking the tray with the cart.

In some embodiments, as shown in FIG. 39, a flowchart of the steps/logic that the processor 210 of FIG. 38 undergoes to display the status of the time that the endoscope is stored and for locking and unlocking the tray in the cart. In this way, a long standing or expired reprocessed endoscope cannot be used as the system will have a lock out feature to lock a specific tray or cart, and a user will have to enter an override identifier or password to remove the specific tray that has been locked in order to reprocess the endoscope again. This ensures that an expired endoscope cannot be used.

The first step 212 is to start or initiate the program. The next step 214 is to input data on the reprocessed endoscope and tray. The next step 216 the logic will verify with the user that the data entered is correct. If the data is correct, in the next step 218, the computer will unlock a specific slot of the cart. The next step 220, the computer will indicate on the display, which can be on the tray, cart, computer, slot and/or housing, to load the tray into the slot. The next step 222, the computer will start the timer after the tray is loaded into the slot. This can be done automatically by the computer or manually by the user. The next step 224 is to indicate a time count. The next step 226 is to indicate on the display the time, which will be done by the computer or may operate independent of the computer (e.g., by a separate timer). The next step 228, the processor will determine if the time expiration is approaching. The next step 230, the processor will indicate this on the display. The next step 232 is for the processor to determine if the time is expired. The next step 234 is to indicate on the display that the time is expired. The next step 236 is to lock a specific tray on which the time has expired. The next step 238 is to indicate on display that the tray is locked into the slot and the last step 240, the program will end.

Figure 40:
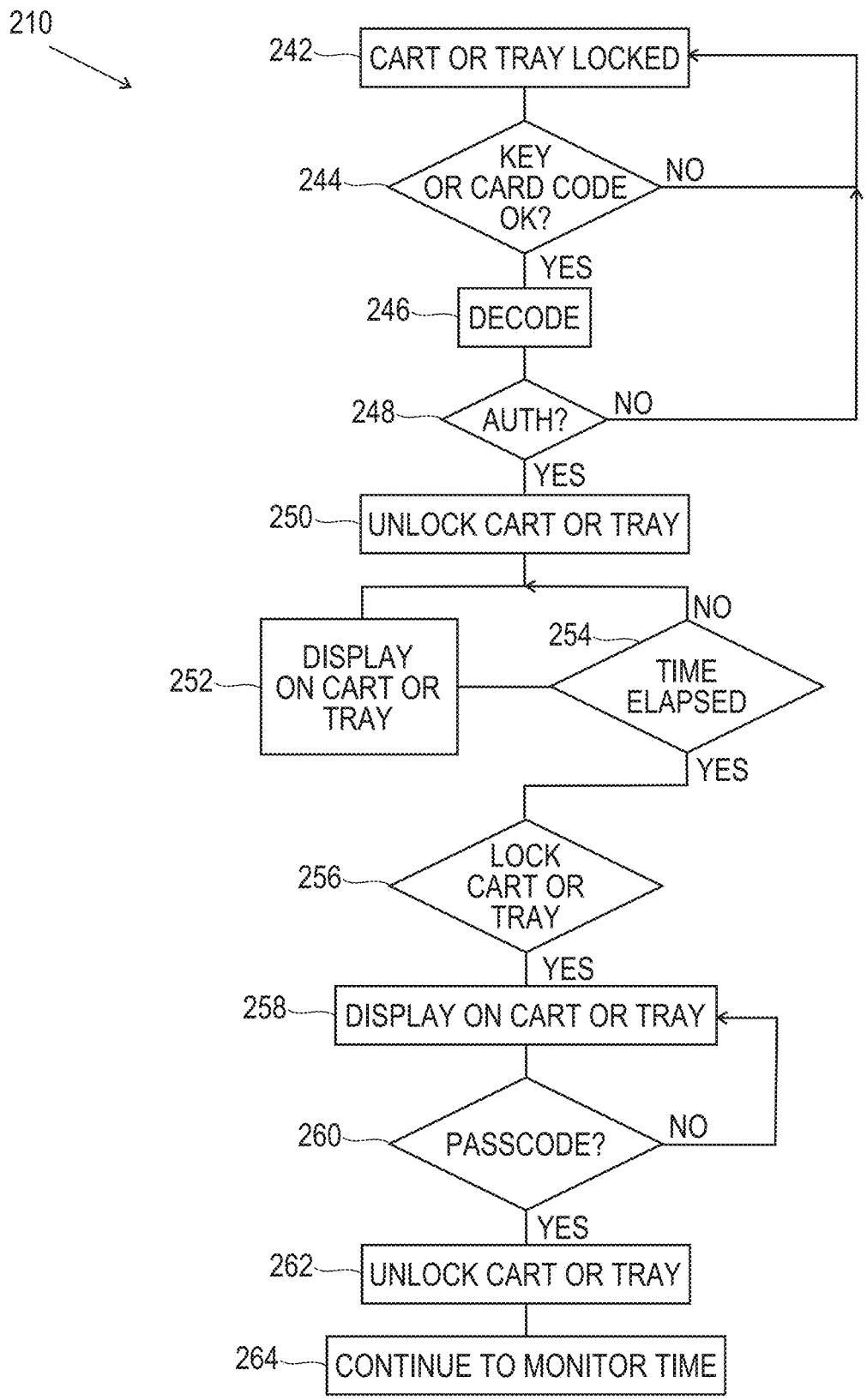
FIG. 40 illustrates a flowchart of the steps/logic that a processor undergoes to lock and unlock the tray into the cart.

In some embodiments, as shown in FIG. 40, a flowchart illustrates the steps/logic that the processor may undergo to lock and unlock a specific tray into the cart. The computer will be coupled to the lock wirelessly or it can be wired to the lock.

In some embodiments the cart can be battery operated or plugged into a wall that has a power outlet. In some embodiments, the cart or tray will be initially in a locked condition 242. The cart can be unlocked with coded signals 244 from an authorized user using a pass key or proximity card, when swiped past the proximity reader on the cart. If a proper coded signal is present, it is decoded 246, and is compared with the authorized code or codes stored in the computer 248. If the code matches one of the authorized unlock codes, the computer actuates the locking surfaces to unlock the cart or tray 250, or otherwise, the cart remains locked or is re-locked 242. It is then displayed on the cart or the tray that the cart or the tray is unlocked 252 via the indicia, such as a green light. If the time has not elapsed 254 for the reprocessed endoscope to be reprocessed, then the cart or tray can remain unlocked 250. If the time has elapsed 254, then the system will perform a lock-down of the cart or tray 256. It is then displayed on the cart or tray that the cart or tray is locked 258 via the indicia, such as a red light. When the user returns to the cart, use of the passkey or proximity card 260 will unlock 262 the cart or tray. The computer will continue to monitor time 264.

In some embodiments, components of the system described above including the cart or tray may be made by injection molding, compression molding, blow molding, thermoforming, die pressing, slip casting, electrochemical machining, laser cutting, water-jet machining, electrophoretic deposition, powder injection molding, sand casting, shell mold casting, plaster-mold casting, investment casting, vacuum casting, permanent-mold casting, slush casting, pressure casting, die casting, centrifugal casting, squeeze casting, rolling, forging, swaging, extrusion, shearing, spinning, or combinations thereof.

In some embodiments, the components of the system may be formed by 3D printing. The terms "three-dimensional printing system," "three-dimensional printer," and "printing," describe various solid freeform fabrication techniques for making three-dimensional articles or objects by selective deposition, jetting, fused deposition modeling, multi-jet modeling, and other additive manufacturing techniques now known in the art or that may be known in the future that use a build material or ink to fabricate three-dimensional objects.

Instructions in the form of schematics encompassing any of the embodiments disclosed herein may be given to a computer to be carried out by a 3D printer. In some embodiments, components of the system may be color coded to signify various properties.

Components of the system may be sterilizable. In various embodiments, one or more components of the system are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the system. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the system, including, but not limited to, gas sterilization, such as, for example, with ethylene oxide or steam sterilization.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. A cart for storage of an endoscope, the cart comprising a housing having a runner assembly configured to receive a tray, the tray configured to store an endoscope; and a timer coupled to the housing, and/or tray, the timer configured to display increments of time that the endoscope is stored in the tray.

2. The cart of claim 1, wherein the tray corresponds to a particular runner assembly of the cart and the runner assembly corresponds to a particular tray.

3. An endoscope storage system, the system comprising a cart comprising a housing having a slot configured to slidably receive a disposable tray, the disposable tray configured to store an endoscope, and a timer coupled to the housing, slot and/or disposable tray, the timer configured to display increments of time that the endoscope is stored in the disposable tray; a disposable liner; and a disposable cover, the disposable liner and disposable cover configured to engage the disposable tray.

4. The system of claim 3, wherein the disposable liner contacts a bottom surface of the disposable tray and at least partially encloses a reprocessed endoscope.

5. The system of claim 3, wherein the disposable cover at least partially encloses a reprocessed endoscope and the disposable tray.

6. The system of claim 3, wherein the disposable cover is a reversible pouch.

7. A method for storing a reprocessed endoscope, the method comprising placing a tray into an endoscope storage cart, the endoscope storage cart comprising a housing having a slot configured to slidably receive the tray, the tray for storing the reprocessed endoscope; and activating a timer coupled to the housing, slot and/or tray, the timer configured to display increments of time that the reprocessed endoscope is stored in the tray.

8. The method of claim 7, wherein the reprocessed endoscope is at least partially enclosed by a disposable liner and the tray is covered by a disposable cover.

9. The method of claim 8, wherein the timer is manually activated by the user after the slot slidably receives the lined and covered tray.

* * * * *